(12) United States Patent
Burbank et al.

(10) Patent No.: US 11,896,750 B2
(45) Date of Patent: Feb. 13, 2024

(54) FILTRATION SYSTEM FOR PREPARATION OF FLUIDS FOR MEDICAL APPLICATIONS

(71) Applicant: NxStage Medical, Inc., Lawrence, MA (US)

(72) Inventors: Jeffrey H. Burbank, Manchester, MA (US); Dennis M. Treu, Castle Rock, CO (US); Goetz Friederichs, Beverly, MA (US); Brian C. Green, Westford, MA (US); Christopher S. Mcdowell, Murray, UT (US); James M. Brugger, Newburyport, MA (US)

(73) Assignee: NxStage Medical, Inc., Lawrence, MA (US)

( * ) Notice: Subject to any disclaimer, the term of this patent is extended or adjusted under 35 U.S.C. 154(b) by 100 days.

(21) Appl. No.: 17/212,866

(22) Filed: Mar. 25, 2021

(65) Prior Publication Data

US 2021/0205519 A1    Jul. 8, 2021

Related U.S. Application Data

(63) Continuation of application No. 16/423,214, filed on May 28, 2019, now Pat. No. 10,973,969, which is a
(Continued)

(30) Foreign Application Priority Data

Jan. 7, 2005    (WO) ................. PCTUS0500381

(51) Int. Cl.
*A61M 1/16*    (2006.01)
*A61M 1/28*    (2006.01)
(Continued)

(52) U.S. Cl.
CPC ............ *A61M 1/1656* (2013.01); *A61M 1/14* (2013.01); *A61M 1/166* (2014.02); *A61M 1/167* (2014.02);
(Continued)

(58) Field of Classification Search
CPC ...... A61M 1/1656; A61M 1/14; A61M 1/166; A61M 1/1668; A61M 1/167;
(Continued)

(56) References Cited

U.S. PATENT DOCUMENTS 2,995,334 A    8/1961    Henderson et al.
3,034,085 A    5/1962    Pauler et al.
(Continued)

FOREIGN PATENT DOCUMENTS

DE    8305713 U1    12/1985
DE    19704564 A1    8/1998
(Continued)

OTHER PUBLICATIONS

"Operator's Manual, Fresenius 2008H Hemodialysis Machine," p. 135. Accessed Jun. 24, 2012. http://www.fmcna.com/documents/2008H_Op_Manual_RevH.pdf.
(Continued)

*Primary Examiner* — Krishnan S Menon
(74) *Attorney, Agent, or Firm* — Potomac Law Group, PLLC

(57) ABSTRACT

A fluid treatment plant has a filter module including at least a first filter and a second filter connected in series and connectable to a supply of fluid. A pump is fluidly connected to the filter module and a controller with a fluid quality sensor is connected to detect a quality of the fluid between the first filter and the second filter. A filter module detector is connected to the controller configured to uniquely detect a filter module connected to the pump, and the controller is
(Continued)

controls the pump responsively to a signal from the fluid quality sensor and the module detector. The controller is configured to continue pumping based on output of the quality sensor and/or based on output from the filter module detector.

18 Claims, 19 Drawing Sheets

Related U.S. Application Data continuation of application No. 15/615,655, filed on Jun. 6, 2017, now Pat. No. 10,420,871, which is a continuation of application No. 11/813,472, filed as application No. PCT/US2006/000608 on Jan. 9, 2006, now Pat. No. 9,700,663.

(51) Int. Cl.
*A61M 1/14* (2006.01)
*A61M 1/34* (2006.01)
*C02F 1/44* (2023.01)

(52) U.S. Cl.
CPC ........ *A61M 1/1668* (2014.02); *A61M 1/1672* (2014.02); *A61M 1/1674* (2014.02); *A61M 1/288* (2014.02); *A61M 1/3462* (2013.01); *C02F 1/44* (2013.01); *A61M 1/28* (2013.01); *A61M 2205/12* (2013.01)

(58) Field of Classification Search
CPC .. A61M 1/1672; A61M 1/1674; A61M 1/288; A61M 1/3462; A61M 1/28; A61M 2205/12; C02F 1/44
See application file for complete search history.

(56) References Cited

U.S. PATENT DOCUMENTS

| | | |
|---|---|---|
| 3,100,486 A | 8/1963 | Nehring |
| 3,103,335 A | 9/1963 | Martinez |
| 3,252,124 A | 5/1966 | Roger |
| 3,709,365 A | 1/1973 | Czaplinski et al. |
| 3,882,020 A | 5/1975 | Cere |
| 4,059,512 A | 11/1977 | Harris |
| 4,144,884 A | 3/1979 | Tersteegen et al. |
| 4,202,332 A | 5/1980 | Tersteegen et al. |
| 4,246,101 A | 1/1981 | Selby |
| 4,370,983 A | 2/1983 | Lichtenstein |
| 4,431,545 A | 2/1984 | Pall et al. |
| 4,432,765 A | 2/1984 | Oscarsson |
| 4,495,067 A | 1/1985 | Klein et al. |
| 4,564,132 A | 1/1986 | Lloyd-Davies |
| 4,596,550 A | 6/1986 | Troutner |
| 4,623,450 A | 11/1986 | Vantard et al. |
| 4,626,240 A | 12/1986 | Edelman et al. |
| 4,628,186 A | 12/1986 | Bergemann et al. |
| 4,643,389 A | 2/1987 | Elson et al. |
| 4,661,246 A | 4/1987 | Ash |
| 4,702,829 A | 10/1987 | Polaschegg et al. |
| 4,711,715 A | 12/1987 | Polaschegg |
| 4,753,371 A | 6/1988 | Michielin et al. |
| 4,772,390 A | 9/1988 | Kawai et al. |
| 4,784,495 A | 11/1988 | Jonsson et al. |
| 4,784,768 A | 11/1988 | Mathieu |
| 4,904,383 A * | 2/1990 | Auerswald ............... B01J 39/05 210/283 |
| 5,032,265 A | 7/1991 | Jha et al. |
| 5,079,236 A | 1/1992 | Drizen et al. |
| 5,102,399 A | 4/1992 | Chu |
| 5,139,483 A | 8/1992 | Ryan |
| 5,178,763 A | 1/1993 | Delaunay |
| 5,221,483 A | 6/1993 | Glenn et al. |
| 5,259,954 A | 11/1993 | Taylor |
| 5,308,333 A | 5/1994 | Skakoon |
| 5,368,555 A | 11/1994 | Sussman et al. |
| 5,423,768 A | 6/1995 | Folden et al. |
| 5,484,431 A | 1/1996 | Scharf et al. |
| 5,511,875 A | 4/1996 | Jonsson et al. |
| 5,536,412 A | 7/1996 | Ash |
| 5,591,344 A | 1/1997 | Kenley et al. |
| 5,616,305 A | 4/1997 | Mathieu |
| 5,622,626 A | 4/1997 | Matkovich et al. |
| 5,645,734 A | 7/1997 | Kenley et al. |
| 5,662,642 A | 9/1997 | Isono et al. |
| 5,690,831 A | 11/1997 | Kenley et al. |
| 5,702,597 A | 12/1997 | Chevallet et al. |
| 5,707,038 A | 1/1998 | Cocatre-Zilgien |
| 5,779,905 A | 7/1998 | Morandi et al. |
| 5,782,762 A | 7/1998 | Vining |
| 5,846,419 A | 12/1998 | Nederlof |
| 5,919,357 A | 7/1999 | Wilkins et al. |
| 5,951,863 A | 9/1999 | Kruger et al. |
| 5,972,223 A | 10/1999 | Jonsson et al. |
| 5,972,225 A | 10/1999 | Karras et al. |
| 6,039,877 A | 3/2000 | Chevallet et al. |
| 6,044,691 A | 4/2000 | Kenley et al. |
| 6,106,723 A | 8/2000 | Grandics et al. |
| 6,132,616 A | 10/2000 | Twardowski et al. |
| 6,136,201 A | 10/2000 | Shah et al. |
| 6,146,536 A | 11/2000 | Twardowski |
| 6,187,207 B1 | 2/2001 | Brauer |
| 6,253,567 B1 | 7/2001 | Imanari et al. |
| 6,254,567 B1 | 7/2001 | Treu et al. |
| 6,280,632 B1 | 8/2001 | Polaschegg |
| 6,284,142 B1 | 9/2001 | Muller |
| 6,287,516 B1 | 9/2001 | Matson et al. |
| 6,299,769 B1 | 10/2001 | Falkvall et al. |
| 6,331,252 B1 | 12/2001 | Sayyid et al. |
| 6,406,631 B1 | 6/2002 | Collins et al. |
| 6,428,518 B1 | 8/2002 | Brengle et al. |
| 6,475,385 B1 | 11/2002 | Boyce et al. |
| 6,485,649 B1 | 11/2002 | Terävä et al. |
| 6,561,997 B1 | 5/2003 | Weitzel et al. |
| 6,572,576 B2 | 6/2003 | Brugger et al. |
| 6,579,253 B1 | 6/2003 | Burbank et al. |
| 6,582,385 B2 | 6/2003 | Burbank et al. |
| 6,589,482 B1 | 7/2003 | Burbank et al. |
| 6,595,943 B1 | 7/2003 | Burbank |
| 6,607,697 B1 | 8/2003 | Müller |
| 6,626,857 B1 | 9/2003 | Ohta et al. |
| 6,638,477 B1 | 10/2003 | Treu et al. |
| 6,638,478 B1 | 10/2003 | Treu et al. |
| 6,649,063 B2 | 11/2003 | Brugger et al. |
| 6,691,058 B2 | 2/2004 | Blakley |
| 6,743,193 B2 | 6/2004 | Brugger et al. |
| 6,745,903 B2 | 6/2004 | Grandics |
| 6,830,553 B1 | 12/2004 | Burbank et al. |
| 6,852,090 B2 | 2/2005 | Burbank et al. |
| 6,855,122 B1 | 2/2005 | Ohta et al. |
| 6,955,655 B2 | 10/2005 | Burbank et al. |
| 6,962,575 B2 | 11/2005 | Tal |
| 6,982,038 B2 | 1/2006 | Dolecek et al. |
| 7,214,312 B2 | 5/2007 | Brugger et al. |
| 7,226,538 B2 | 6/2007 | Brugger et al. |
| 7,322,969 B2 | 1/2008 | Hattori et al. |
| 7,419,597 B2 | 9/2008 | Brugger et al. |
| 7,473,238 B2 | 1/2009 | Brugger et al. |
| 7,544,300 B2 | 6/2009 | Brugger et al. |
| 8,182,691 B2 | 5/2012 | Stahl |
| 8,545,428 B2 | 10/2013 | Burbank et al. |
| 8,679,348 B2 | 3/2014 | Burbank et al. |
| 9,388,059 B2 | 7/2016 | Burbank et al. |
| 2001/0016699 A1 | 8/2001 | Burbank et al. |
| 2001/0021817 A1 | 9/2001 | Brugger et al. |
| 2001/0037079 A1 | 11/2001 | Burbank et al. |
| 2001/0039441 A1 | 11/2001 | Ash |
| 2001/0048909 A1 | 12/2001 | Taylor |
| 2002/0085952 A1 | 7/2002 | Ellingboe et al. |
| 2002/0104800 A1 | 8/2002 | Collins et al. |
| 2002/0147481 A1 | 10/2002 | Brugger et al. |
| 2002/0162778 A1 | 11/2002 | Peabody et al. |

(56) References Cited

U.S. PATENT DOCUMENTS

| | | |
|---|---|---|
| 2002/0167322 A1 | 11/2002 | He et al. |
| 2002/0190000 A1 | 12/2002 | Baurmeister |
| 2003/0010701 A1 | 1/2003 | Collins et al. |
| 2003/0010717 A1 | 1/2003 | Brugger et al. |
| 2003/0010719 A1 | 1/2003 | Brugger et al. |
| 2003/0042201 A1 | 3/2003 | Sizelove et al. |
| 2003/0051767 A1 | 3/2003 | Coccaro et al. |
| 2003/0080140 A1 | 5/2003 | Neas et al. |
| 2003/0105435 A1 | 6/2003 | Taylor |
| 2003/0130606 A1 | 7/2003 | Tuck |
| 2003/0168389 A1 | 9/2003 | Astle et al. |
| 2003/0173297 A1 | 9/2003 | Grandics |
| 2003/0220598 A1 | 11/2003 | Busby et al. |
| 2003/0236481 A1 | 12/2003 | Burbank |
| 2004/0045881 A1 | 3/2004 | Collins et al. |
| 2004/0060866 A1 | 4/2004 | Radunsky et al. |
| 2004/0069709 A1 | 4/2004 | Brugger et al. |
| 2004/0089594 A1 | 5/2004 | Collins et al. |
| 2004/0186415 A1 | 9/2004 | Burbank et al. |
| 2004/0222139 A1 | 11/2004 | Brugger et al. |
| 2004/0232079 A1 | 11/2004 | Taylor et al. |
| 2005/0010158 A1 | 1/2005 | Brugger et al. |
| 2005/0045548 A1 | 3/2005 | Brugger et al. |
| 2005/0103717 A1 | 5/2005 | Jha et al. |
| 2005/0171501 A1 | 8/2005 | Kelly |
| 2005/0209547 A1 | 9/2005 | Burbank et al. |
| 2005/0215975 A1 | 9/2005 | Mathias et al. |
| 2006/0021944 A1 | 2/2006 | Carson et al. |
| 2007/0007208 A1 | 1/2007 | Brugger et al. |
| 2007/0038191 A1 | 2/2007 | Burbank et al. |
| 2007/0260168 A1 | 11/2007 | Brugger et al. |
| 2008/0053905 A9 | 3/2008 | Brugger et al. |
| 2008/0173574 A1 | 7/2008 | Silveri |
| 2008/0203023 A1 | 8/2008 | Burbank et al. |
| 2008/0210606 A1 | 9/2008 | Burbank |
| 2008/0230450 A1 | 9/2008 | Burbank et al. |
| 2011/0186521 A1 | 8/2011 | Burbank et al. |
| 2012/0074060 A1 | 3/2012 | Lass |
| 2012/0325696 A1 | 12/2012 | Burbank et al. |
| 2013/0327691 A1 | 12/2013 | Burbank et al. |

FOREIGN PATENT DOCUMENTS

| | | |
|---|---|---|
| EP | 0121085 A1 | 10/1984 |
| GB | 2135598 A | 9/1984 |
| JP | 4941276 U | 11/1974 |
| JP | S57211362 A | 12/1982 |
| JP | 2003175101 A | 6/2003 |
| JP | 2004000583 A | 1/2004 |
| WO | 1996036370 A1 | 11/1996 |
| WO | 1999056696 A1 | 11/1999 |
| WO | 2002032476 A2 | 4/2002 |
| WO | 2002095675 A1 | 11/2002 |
| WO | 2003006100 A1 | 1/2003 |
| WO | 2003006139 A1 | 1/2003 |
| WO | 2003103533 A2 | 12/2003 |
| WO | 2004062710 A2 | 7/2004 |
| WO | 2004066121 A2 | 8/2004 |
| WO | 2004080282 A2 | 9/2004 |
| WO | 2004084972 A2 | 10/2004 |
| WO | 2005068043 A1 | 7/2005 |
| WO | 2006074429 A1 | 7/2006 |
| WO | 2007118235 A2 | 10/2007 |

OTHER PUBLICATIONS

"Risk Free Connection of Pre-Sterilized Single Use Fluid Path Assemblies to Stainless Steel SIP Systems with Lynx ST (Steam-to) Connectors." Millipore Corporation Catalogue, May 2003.
Examination Report for European Patent Application No. 03736859.4 dated Nov. 11, 2008.
FDA guidelines for Bacterial Endotoxins/Pyrogens. Accessed Apr. 12, 2010. http://www.fda.gov/ICECI/Inspections/InspectionGuides/InspectionTechnical-Guides/ucm072918.htm.
Final Office Action for U.S. Appl. No. 15/195,801 dated Mar. 9, 2018.
Ledebo, Ingrid, "On-line Preparation of Solutions for Dialysis: Practical Aspects Versus Safety and Regulations." Journal of the American Society of Nephrology, Jan. 1, 2002, 13: pp. S78-S83.
Office Action for U.S. Appl. No. 15/195,801 dated Oct. 23, 2017.
Online encyclopedia article "Depyrogenation." Accessed Apr. 12, 2010. http://en.wikipedia.org/wiki/Depyrogenation.
Shipe, B. "The Case for UV in Dechlorination Applications." Water Conditioning and Purification Magazine, Jan. 2003, 45(1): pp. 34-36.

\* cited by examiner

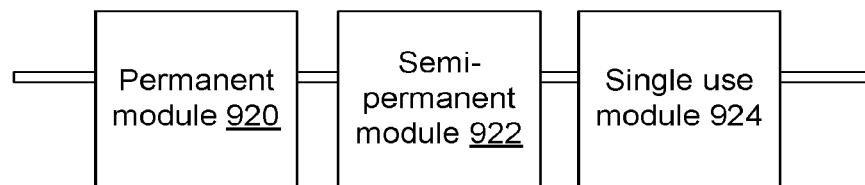
Fig. 1A
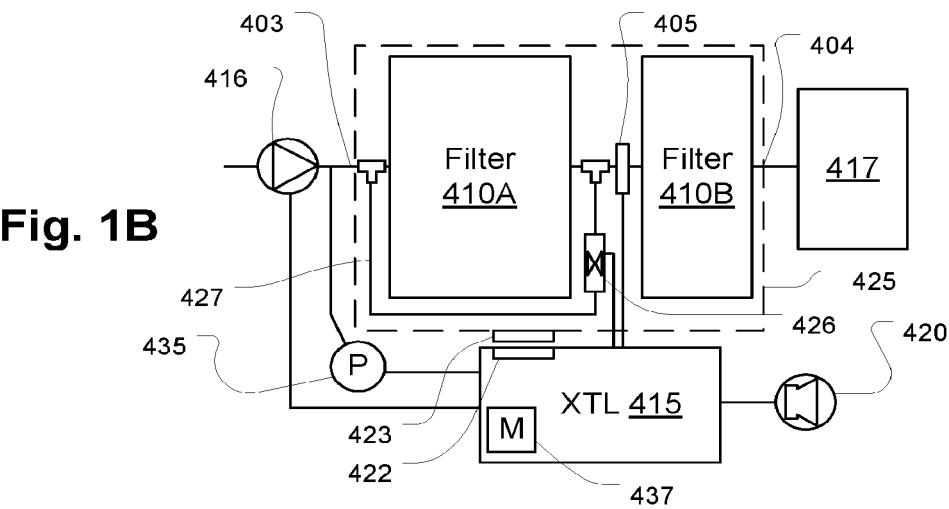
Fig. 1B
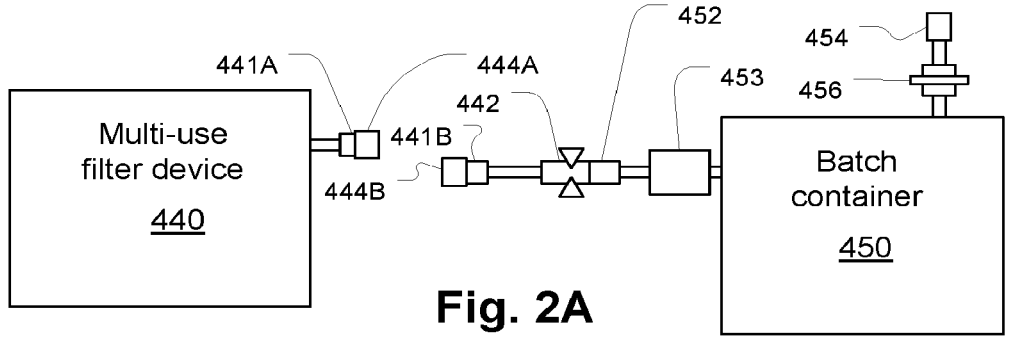
Fig. 2A
Fig. 2B

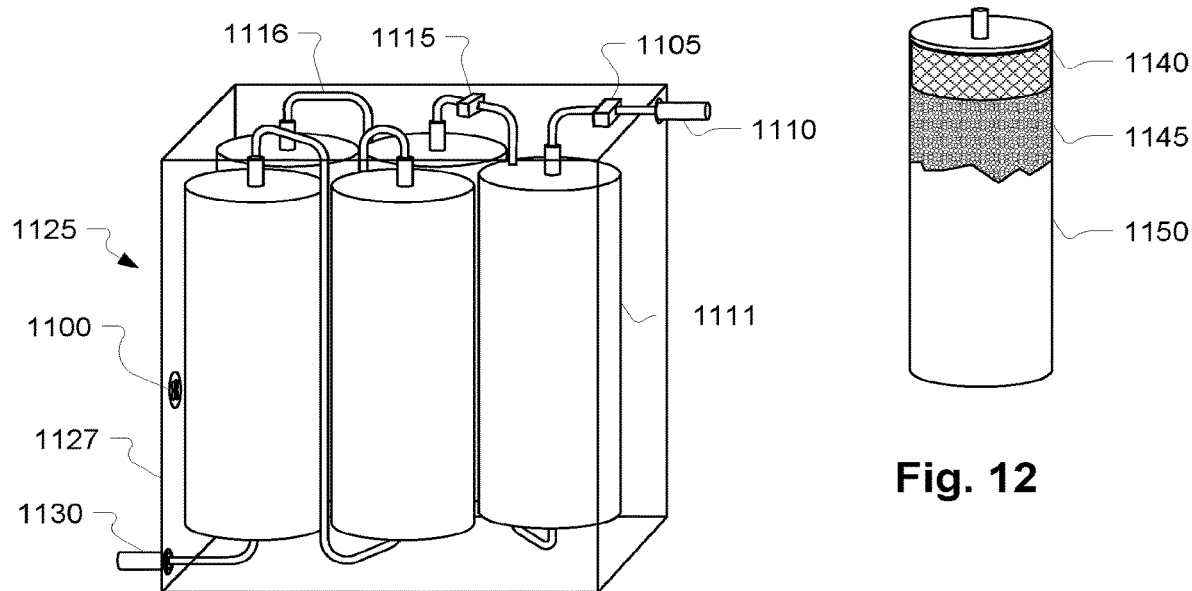
Fig. 11
Fig. 12
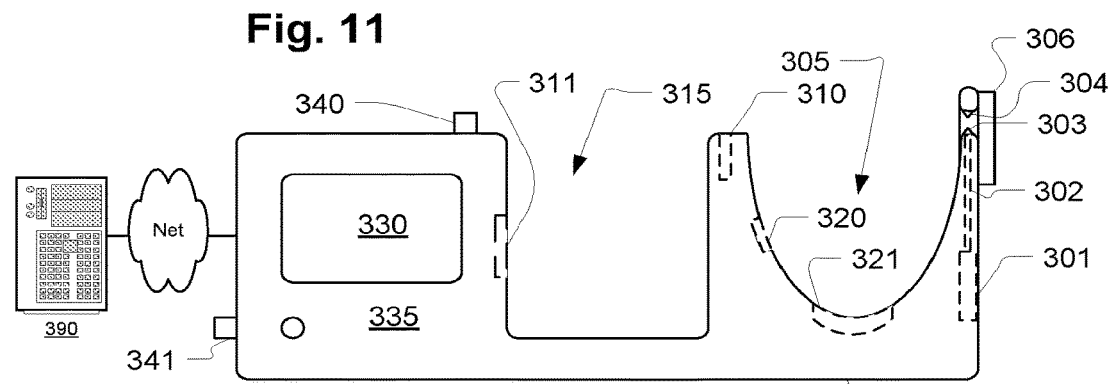
Fig. 13A
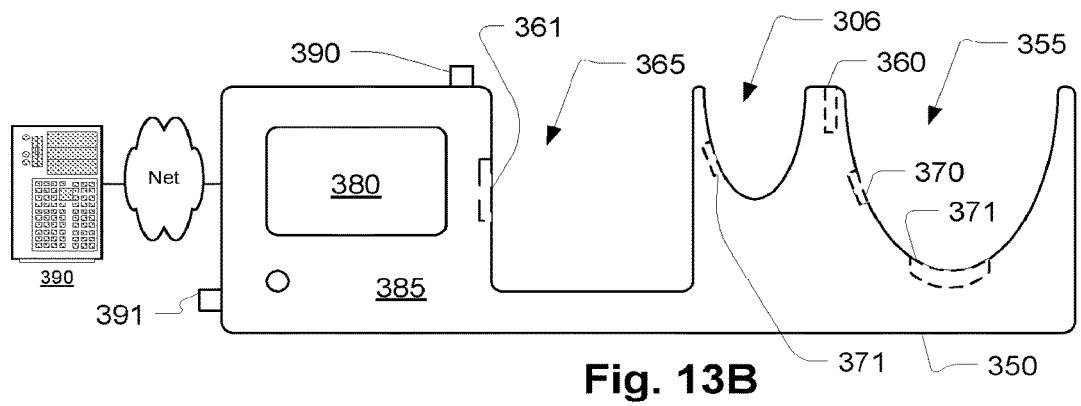
Fig. 13B

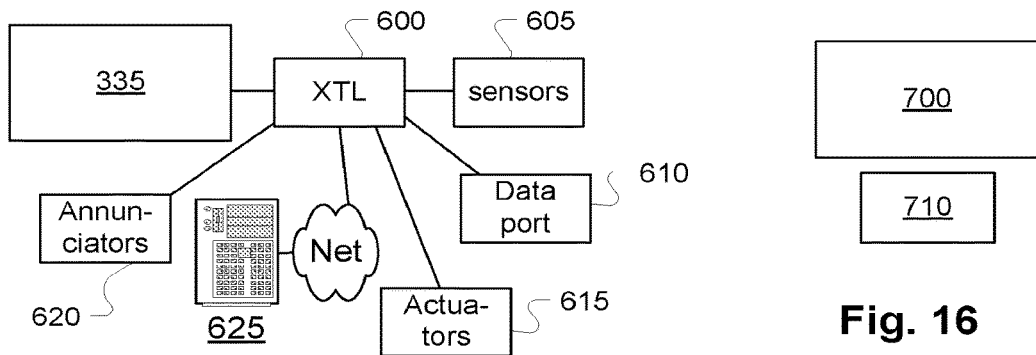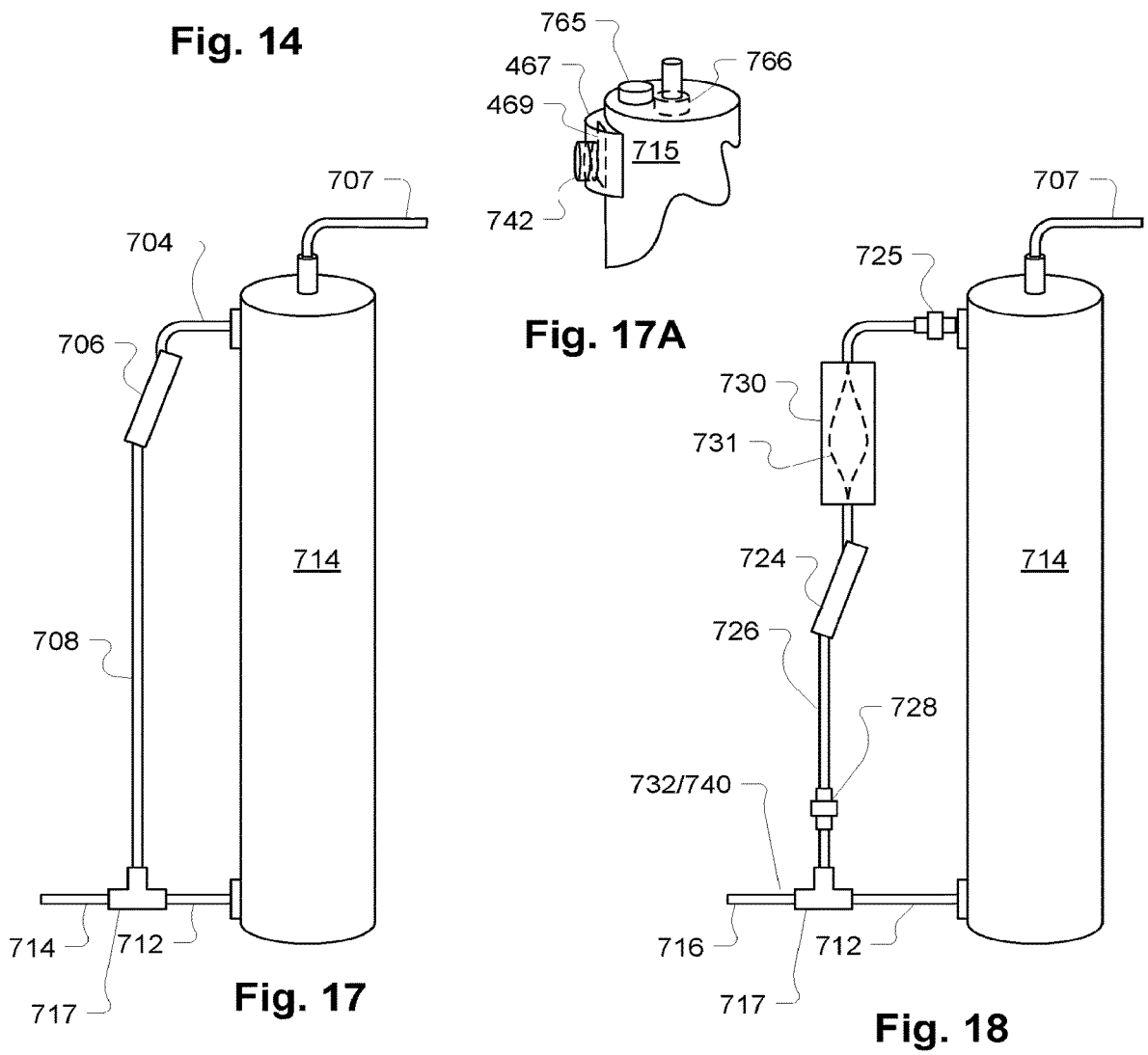

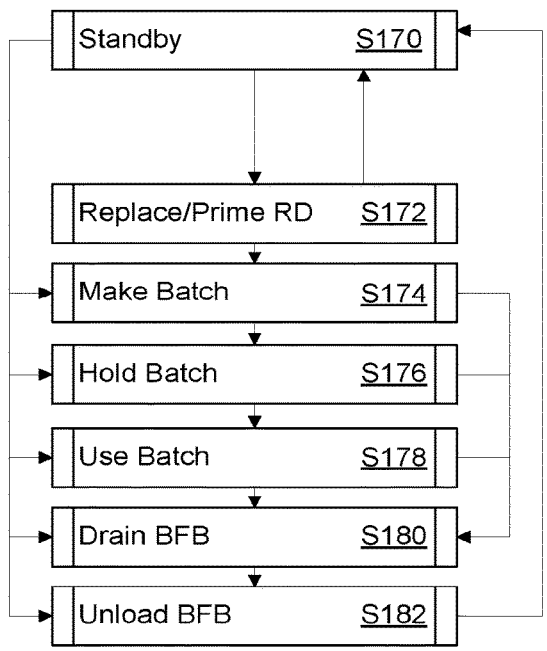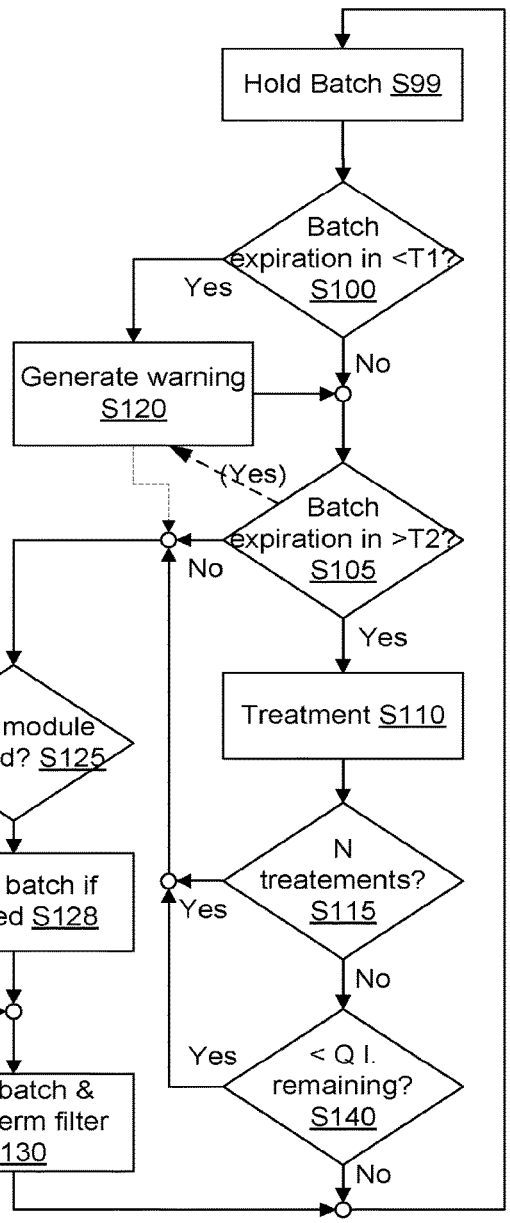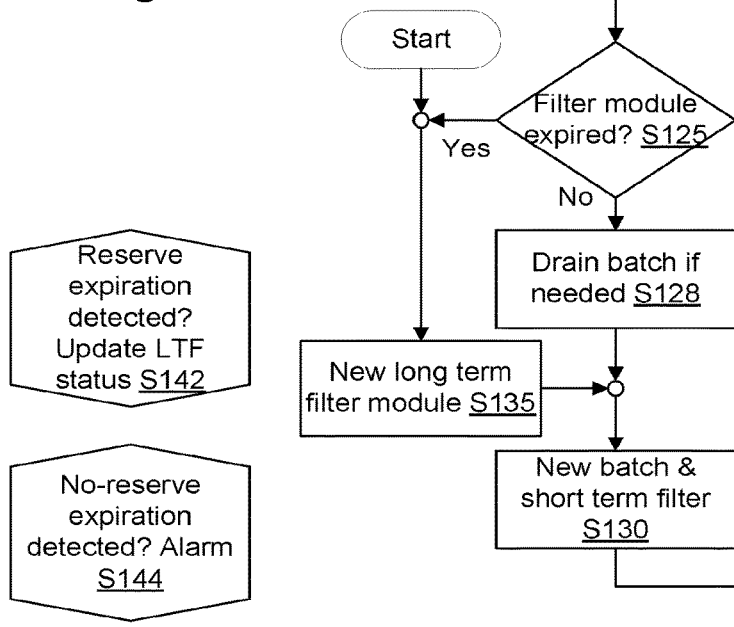
Fig. 20A
Fig. 20B

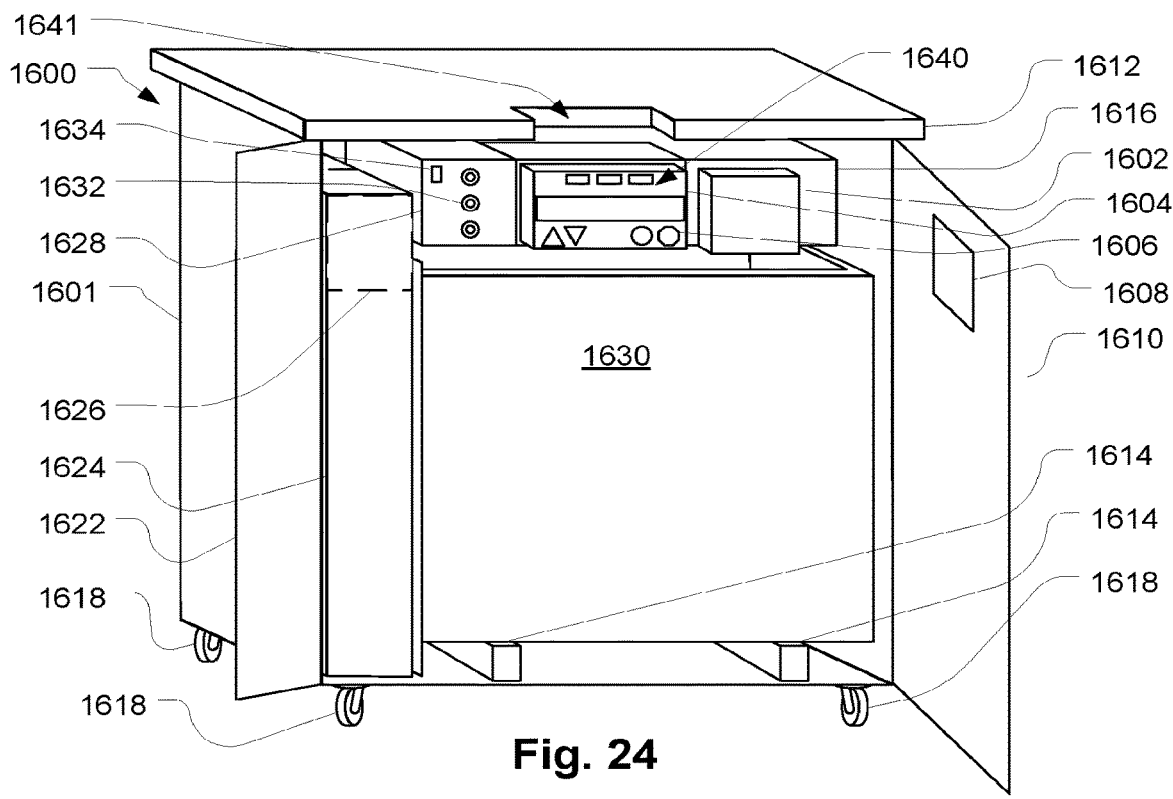
Fig. 24
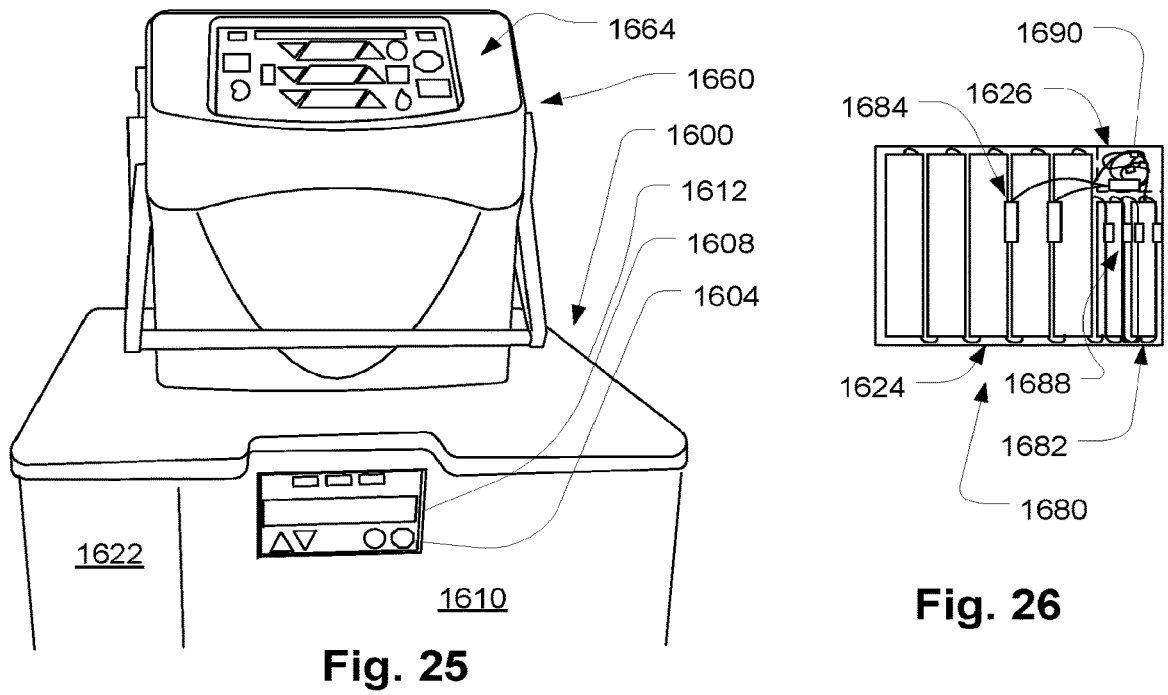
Fig. 25
Fig. 26

FILTRATION SYSTEM FOR PREPARATION OF FLUIDS FOR MEDICAL APPLICATIONS

RELATED APPLICATIONS

The present application is a continuation of U.S. application Ser. No. 16/423,214 filed on May 28, 2019, which is a continuation of U.S. application Ser. No. 15/615,655 filed Jun. 6, 2017, which issued as U.S. Pat. No. 10,420,871 on Sep. 24, 2019, which is a continuation of U.S. application Ser. No. 11/813,472, filed May 12, 2008, which issued as U.S. Pat. No. 9,700,663 on Jul. 11, 2017, which is a national stage entry of International Application No. PCT/US06/00608, filed Jan. 9, 2006, which claims foreign priority to PCT/US05/00381, filed Jan. 7, 2005, all of which applications are incorporated herein by reference in their entireties.

BACKGROUND OF THE INVENTION

Many medical applications require purified water and other fluids, for example, hemofiltration, tissue irrigation, and hemodiafiltration. Some prior art systems have focused on continuous purification processes that require a separate diafiltration/purification apparatus that must be periodically purged and verified to provide sufficient constant flow of sterile replacement fluid. (See Chavallet U.S. Pat. Nos. 6,039,877 and 5,702,597.) Such devices are necessarily complicated and require separate pumping systems for the purification process. In addition, the rate of supply of fluid for such systems is very high, requiring expensive filters to be used. The same high-rate problem exists for the generation of replacement fluid for hemofiltration, and therefore also requires expensive filtering apparatus.

Large and small scale inline systems are known for preparation of infusible fluids and for preparation of dialysate. The following prior art references discuss examples of such systems. US Patent Publication No. 2004/0232079 US Patent Publication No. 2003/0105435; U.S. Pat. Nos. 5,645,734 5,782,762 6,136,201; PURELAB Maxima, Ultra-Pure Water Purification Systems (http://www.elqalabwater.com); Shipe, Brad; "The Case for UV in Dechlorination Applications," Water Conditioning & Purification Magazine, January 2003, Vol 45 No. 1.

BRIEF DESCRIPTION OF THE DRAWINGS

FIG. 1A shows schematically at a high level a water purification system according to embodiments of the disclosed subject matter.

FIG. 1 B illustrates a filter device with control elements that provide assurance of fluid quality and prevent breakthrough of contamination upon filter expiration.

FIGS. 2A and 2B illustrate a filter and batch container with connector systems that ensure against contamination.

FIG. 11 illustrates a filter module in partial ghost perspective view.

FIG. 12 illustrates a filter cartridge with an expansion device.

FIGS. 13A and 13B illustrate fluid preparation devices for use with a replaceable filter module such as the one illustrated in FIG. 11.

FIG. 14 illustrates a control system to support features of various embodiments.

FIG. 16 illustrates a treatment environment for use of a control embodiment.

FIGS. 17, 17A, and 18 illustrate ultrafilter configurations that are tolerant of the evolution of air from within the ultrafilter.

FIGS. 20A and 20B are flow charts illustrating operations of a treatment fluid preparation and storage device according to an embodiment of the invention.

FIGS. 24 and 25 illustrate various mechanical features including a housing for a treatment fluid preparation and storage device according to an embodiment of the invention.

FIG. 26 illustrates a long term disposable filter module for a treatment fluid preparation and storage device according to an embodiment of the invention.

SUMMARY OF SOME EMBODIMENTS

Figure 3:
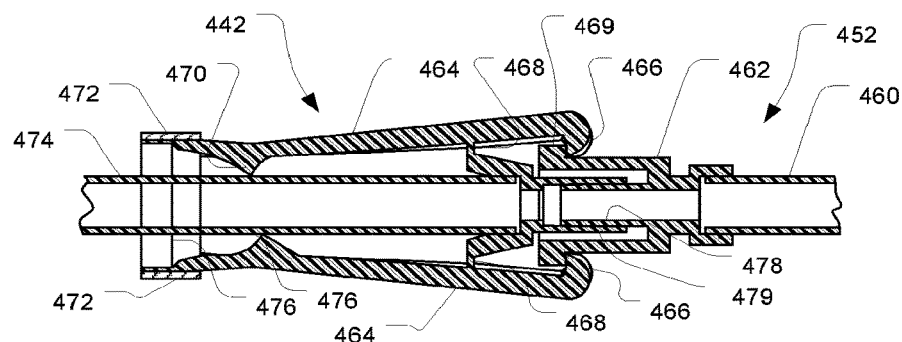
FIG. 3 illustrates a self-clamping connector.

According to an embodiment, the inventions include a medical fluid treatment device, comprising: a housing having water supply and drain connections and an electrical supply connection, a treatment fluid preparation device configured to purify water, and use the purified water to dilute a solute to prepare a batch of a purified water, the batch being contained in a disposable container enclosed in the housing, the batch containing enough treatment fluid to perform multiple renal replacement therapy treatments each being at least a day apart, a heater configured to maintain a temperature of the batch at a temperature for immediate use in renal replacement therapy, a controller configured to indicate at least one of: an indication that the batch has expired, is about to expire, an amount of time before the batch will expire, the controller being configured to make the batch available for multiple treatments, and connections for connecting a renal replacement therapy device to receive contents of the batch.

According to another embodiment, the device is such that the disposable container is a bag and the housing has a tank portion configured to support the bag.

According to another embodiment, the device is such that the bag includes a first filter that is replaced each time the bag is replaced.

According to another embodiment, the device is such that the housing has a table top surface and the table top is configured to support the renal replacement therapy device.

According to another embodiment, the device is such that the housing has a table top surface and a height not greater than 1 m.

According to another embodiment, the device is such that the treatment fluid preparation device includes a disposable filtration module that is replaced one every multiple batches.

According to another embodiment, the device is such that the disposable container is a bag and the housing has a tank portion configured to support the bag, the tank portion being configured as a drawer portion that is hidden behind a door on front of the housing. According to another embodiment, the device is such that the housing has a table top surface and a height not greater than 1 m., the table top is uninterrupted by any fixtures, the controller has a user interface mounted on a front of the housing.

According to another embodiment, the device is such that the housing has a table top surface and a height not greater than 75 cm.

According to another embodiment, the device is such that the disposable container has multiple outlet connections, each configured with a non-reopenable clamp.

According to another embodiment, the device is such that the treatment fluid includes a lactate based dialysate.

According to another embodiment, the device is such that the housing is fitted with wheels.

According to another embodiment, the device is such that the disposable container is a bag and the housing has a recess portion configured to support the bag, the recess having a bottom on which the bag sits, the bottom being at a bottom of the housing and having at least one leak sensor therein.

According to another embodiment, the device is such that the housing has at least one leak sensor outside of any fluid containing or conveying component to detect leaks.

According to another embodiment, the device is such that the controller is configured to empty the batch after use.

According to another embodiment, the device is such that the drain connection includes a Y-junction receiving a connection from the disposable container and a connector for connection to a spent fluid line of the treatment machine.

According to another embodiment, the device is such that one leg of the Y-junction includes a conductivity sensor configured to allow the controller to test a sample of the batch by flushing a portion thereof into the Y-junction.

According to another embodiment, the device is such that the disposable container includes an actuator portion with a filter that is replaced for each batch.

According to another embodiment, the device is such that the treatment fluid preparation device includes a filter that is replaced once every multiple batches.

According to another embodiment, the device further comprises a pump and fluid circuit portion configured to generate a constant pressure for uptake by the treatment device.

According to another embodiment, the device is such that the fluid circuit portion is a feedback loop that returns to the disposable container and includes an inline check valve with a cracking pressure equal to the constant pressure.

According to another embodiment, the device includes a valve actuator assembly configured to draw concentrate from a container and supply the concentrate to the disposable container, to rinse the concentrate container and supply a diluted fluid that results from rinsing the concentrate container to the disposable container.

DETAILED DESCRIPTION

The present disclosure relates to apparatus, methods, devices, articles of manufacture, etc. for producing pure water and, in some embodiments, pure solutions. These may be used for the preparation of solutions for medical applications such as tissue irrigation, preparation of pharmaceutical, blood treatments such as hemofiltration, hemodialysis, hemodiafiltration and ultrafiltration, and other treatments.

As described in FIG. 1A, to supply suitable water that is substantially free of unwanted dissolved and undissolved materials, a combination of permanent and replaceable components may be provided at the treatment site. FIG. 1A is an overview of a framework that provides benefits, particularly in certain environments. One such environment is renal replacement therapy. Patients must be treated at least twice a week and often daily. On the other hand, excellent sterility design urges the use of pre-sterilized throw-away components to ensure against various modes of contamination which need not be enumerated. But replacing every component that must be contamination-free upon every use is profoundly expensive, particularly where treatments are done every day. Prior art approaches have addressed this problem by combining permanent components whose sterility is guaranteed by intensive sterilization procedures, some of which are backed up (made failsafe) by using additional disposable components that are used once and discarded. Alternatively, the disposable can be made more robust to avoid the on-site sterilization procedures. But this presents the problem of forcing the designer to use inexpensive, and therefore less desirable components in the disposable portions, or of simply imposing the burden of high cost on the medical treatment system.

FIG. 1A shows a new model that compromises on this point and is considered particularly applicable in the renal replacement therapy environment. A permanent module 920 has certain pretreatment components that may be used repeatedly without replacement and without sterilization and includes filtration and treatment steps that are not unduly inclined to aggravate, or susceptible to, contamination. Examples are illustrated in the further embodiments. This permanent module may be designed to receive variations of water quality. A semi-permanent module 922 provides more than one use, for example a month's worth of uses, but is disposable periodically or upon detection of incipient failure. The permanent module may contain a controller to enforce the proper use and handling of the semi-permanent module since safeguards must be enforced with regard to it. But with the semi-permanent modules, as discussed below in connection with particular embodiments, the procedures do not involve washing, cleansing, sterilization. The final stage includes final filtration and/or treatment steps provided in a single-use element 924. In the final stage, the least expensive components may be arranged to guard against sterility failures of the upstream components. As will be seen, the preferred embodiments described herein conform to this model. Variations of the model are possible including fragmenting the intermediate modules into ones used according to other schedules such as one module replaced monthly and another replaced weekly. An example of a semi-permanent element and a control system to safeguard against contamination are shown in FIG. 1B. Note that the embodiment of FIG. 1B may constitute an independent invention and need not be employed in a combination as discussed with reference to FIG. 1A, although this identified as a preferred configuration. Referring to FIG. 1B, a pump 416 feeds raw water into a filter module 425 via an input line 403. The filter module 425 contains first and second filters 410A and 410B. In an embodiment, the first and second filter stages 410A and 410B are deionizing filters. The first and second filter stages 410A and 410B may be accompanied by other types of filters (not shown here but discussed and illustrated elsewhere in the instant specification) in the filter module or externally thereto to perform a complete water treatment. Treated water is supplied to a batch container 417, which may or may not be present. In the illustrated configuration, water is treated for preparation of a medicament which may be included in concentrate form in the batch container 417 as a presterilized consumable unit.

Between the first and second filter stages 410A and 410B, a water quality sensor 405 is provided. In an embodiment, the water quality sensor 405 is a conductivity or resistivity probe that detects ionic species in the water after passing through the first stage filter 410A. In a preferred embodiment, the second stage 410B provides at least some redundancy in that the second stage 410B provides some of the filtration effect of the first stage 410A. In an alternative embodiment it provides all of the filtration of the first stage 410A and is thereby completely redundant. In such an arrangement, the first stage would expire (become depleted), allowing contaminants to break through, before the second stage expires. The contaminant breakthrough is detected by a controller 415 connected to the water quality sensor 405. The controller 415 also controls the pump 416. Upon expiration of the first stage 410A, the controller allows the preparation to continue until a certain amount of fluid is collected in batch container 417, preferably an amount required for a treatment. Once this threshold quantity is delivered, the controller will not allow the pump 416 to be started until the filter module 425 is exchanged with a fresh one. The second stage filter 410B, preferably, is sized to ensure that, by itself, it can purify at least a single batch of water, plus a safety margin without any contaminant breakthrough to the output line 404. In a preferred embodiment, the second stage filter 410B is a smaller size than the first 410A. In the preferred embodiment, the second stage filter 410B may be of a different type which may not be as able to handle high contamination loads as the first 410A. This may be acceptable because, although after breakthrough is detected, the emerging fluid is still substantially purified and the load input to the second stage filter 410B may remain low until a single batch of fluid is prepared.

In an alternative embodiment, the filter module 425 is provided with a permanently attached data carrier 423 such as radio frequency identification device (RFID), bar code (1- or 2-dimensional), contact-type identification device, etc. The data carrier 423 contains a unique identifier of the filter module. When a cartridge is connected to the pump, the controller 415 reads the data carrier 423 using a reader device 422 and stores the identifier in a memory 437. If the water quality sensor 405 indicates contaminant breakthrough, the controller permanently stores the identifier in an expired directory in the memory, which has a non-volatile portion for the directory. If a user attempts to connect a module 425 with an identifier stored in the directory, the controller will not operate the pump and will indicate the error condition by means of an annunciator 420 or equivalent device, such as an LCD display message.

Note that in an alternative device, the data carrier 423 is a programmable device with a writable memory. In this embodiment, the controller 415 programs the data carrier 423 with a flag indicating that the filter module 425 is expired. The controller 415 then prevents the initiation of a new batch.

FIG. 1 B also illustrates an optional embodiment with a pressure transducer 435 that may be used to test for clogging of the first stage filter 410A. When the pump 416 head pressure reaches a particular maximum, in order to allow a batch preparation to be completed, the controller activates a normally-closed valve 426 to bypass the first filter stage 410A. Water flows through a bypass line 427 and through the second stage filter 410B. The expiration of the filter module 425 may then be enforced by the controller in either of the ways described above. The above embodiment may be used in filter modules 425 that contain filters that clog when depleted such as carbon filters or porous membrane filters. Not that the clogging and breakthrough devices described above may be combined or used exclusively in a given filter module embodiment. Note also that the head pressure may be sampled and stored over a period of time to determine if the pressure change profile is characteristic of a filter suffering normal usage. This would distinguish, for example, an accidental line blockage and prevent inappropriate use of the bypass line 427.

Referring to FIGS. 2A and 2B, a multi-use filter device 440 has an outlet port 441A with a cap 444A to avoid contamination. The outlet port 441A is connectable to a mating port 441 B, which is also capped (cap 444B). The ports 441 A and 441 B may be, for example, locking luer connectors. A special clamping connector 442, which seals itself when disconnected from a mating connector 452 is connected to port 441 B and a line connecting it to a batch container 450 which receives purified water from the multi-use filter device 440. A microporous filter 453 guards against the introduction of contaminants by touch contamination when connectors 441 A and 441 B are mated.

The special clamping connector 442 may any suitable device that seals off, to prevent contamination. An embodiment of such a connector is shown in FIG. 3, although the sealing and disconnecting functions, to be described below, can be performed by separate mechanisms so this embodiment is not essential. An outlet tube 460 connectable to the filter 453 of FIG. 2A is permanently affixed to a male luer fitting 478 of a male connector 452 that is received by a female luer fitting 479 of a female connector 442. The female connector 442 has a pair of latch arms 464 that engage a ridge 469 of the male connector 452. The latch arms 464 pivot on living hinges 468 affixed to the female luer fitting 479. Pinching ridges 470 and 476 compress the tube 474 when a bendable retaining ring 472 is squeezed. At the same time, engaging ends 466 of the latch arms 464 retract from the ridge 469 releasing the male luer connector 452. The bendable retaining ring 472 retains its deformed shape once it is pinched so that the tube 474 remains pinched and thereby sealed when the connectors 442 and 452 are disconnected. The bendable retaining ring 472 may be made of ductile metal, for example. The retaining ring 472 may be replaced by another suitable device such as a ratchet mechanism.

Returning to FIGS. 2A and 2B, when the multi-use filter device 440 is first used, its outlet connector 441A is sealed with a cap 444A as is the inlet connector 442 (with cap 444B) of the batch container 450. The batch container 450 may be sealed and sterilized with the special fitting 442 and its mating connector 452, which may correspond to elements 442 and 452 in FIG. 3, connected in a completely sealed and pre-sterilized state. Other ports such as a sampling port 454 may also be sealed and, if only used as outlets, protected from intrusion of fluid by means of a check valve 456 and/or another membrane filter 453 (not shown separately). The first time the batch container 450 is connected to the multi-use filter device, the caps 444A and 444B are removed and the connectors 441 A and 441 B mated. After filtered water is collected in the batch container 450, the special clamping connector 442 is disconnected and left connected to the multi-use filter device 440 to keep it sealed and free from contamination as shown in FIG. 2B. The second time the multi-use filter device 440 is used, the special clamping connector 442 is removed by means of the connector pair 441 A and 441 B and discarded while a new batch container's 450 connector 441 B is mated to the pre-existing multi-use filter device's 440 outlet connector 441 A. The connector 441 B carries a new special clamping connector 442 and the same process can be repeated.

Figure 4:
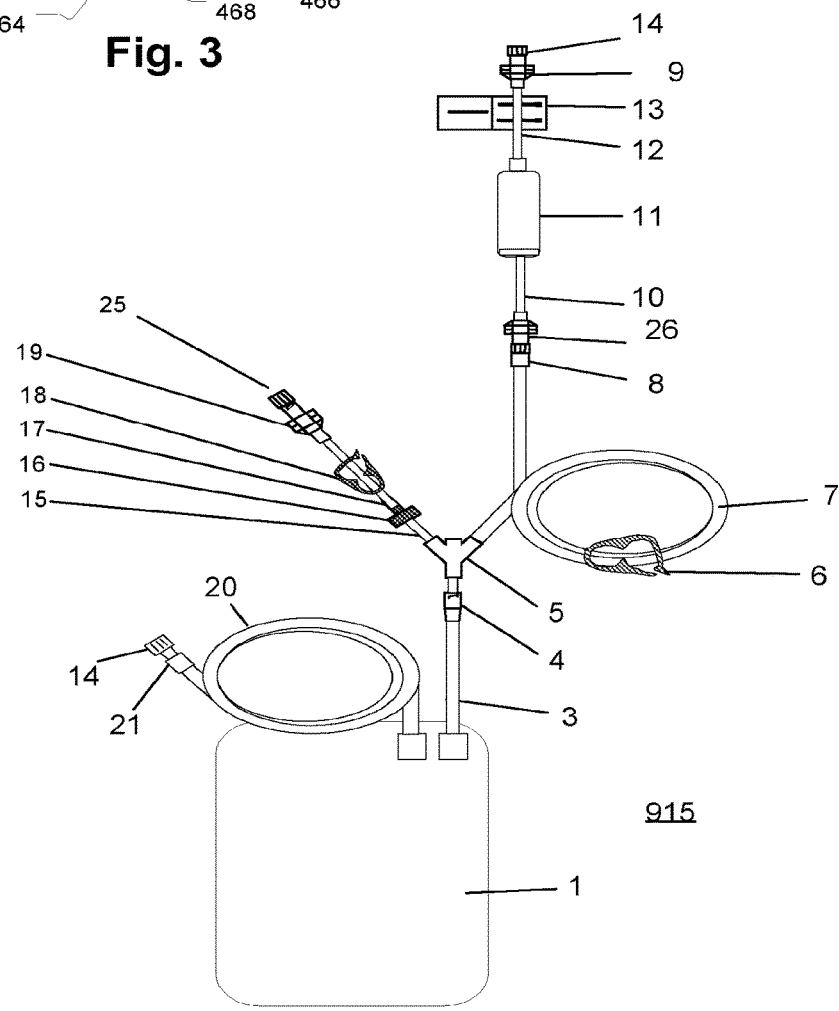
FIG. 4 illustrates a batch container tubing set.

FIG. 4 shows an embodiment of a batch container, for example one that may be used with the foregoing embodiments, but in particular, with the above embodiments. The batch container 1 has a batch container, proper, 1, a break-off female luer lock connector 4, a y-connector, 5, a pinch clamp 6, a male luer 8, a female luer 26, a sterile filter (e.g., 0.22 micron pore or pyrogen filter) 11, a non-reopenable tubing clamp 13, a non-breathing cap 14 on a female luer 9. Line 15 has an in-line check valve 16, a pinch clamp 18, a break-off male luer cap 25 and female luer 19, and a female luer 21. Various tubing branches 3, 7, 10, 12, 15, 17, and 20 connect these elements. The batch container 1 is delivered to a patient treatment setting as a sealed sterile container with all terminals sealed. The batch container 1 may contain, as delivered, a concentrate solution sufficient to create a treatment batch of fluid, such as dialysate or replacement fluid, when water is added. Concentrate may be added by means of the luer connector 21. In the tubing set delivered to the treatment site, the tubing branch 20 may be sealed and cut after the concentrate is added. Water is added at the treatment site through connection to a water source via luer 9. The water is preferably metered to provide a predefined quantity. The sterile filters should be sufficient to protect against contamination by pyrogens before water is added to the batch container 1. A sample of diluted treatment fluid may be drawn through the luer 19 before treatment. The check valve 16 prevents any contamination due to backflow from the sampling procedure. After water is added to the treatment fluid container 1, the luer 9 is disconnected from the male luer 8 and the male luer connector connected to the blood treatment system. Luer connectors are shown by way of example as are other features and these are not essential to all embodiments.

Figure 5:
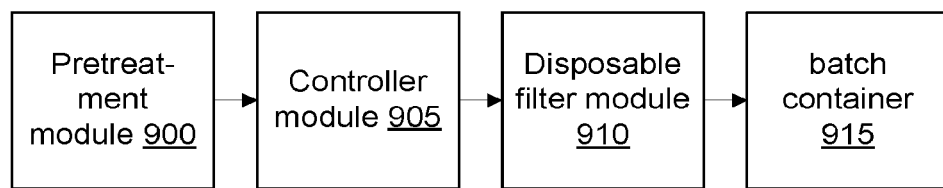
FIG. 5 illustrates a fluid preparation apparatus embodiment in a figurative way for discussing various features and arrangements of a water purification system.

FIG. 5 illustrates another arrangement of a particular embodiment whose description follows. A pretreatment module 900 provides primary filtration from a raw water supply, for example tap water and feeds prefiltered water to a controller module 905 which provides various control functions, a pump, pressure detection and control, and permanent filtering capabilities which are not shown separately here. Water is metered by the control module into a consumable disposable module 910 which may provide deionization, adsorption filtration, microporous filtering, chemical pretreatment, etc. and any other types of filtering that may require replacement of components. The purified water is finally conveyed to the batch container circuit 915 discussed with reference to FIG. 4.

Figure 6:
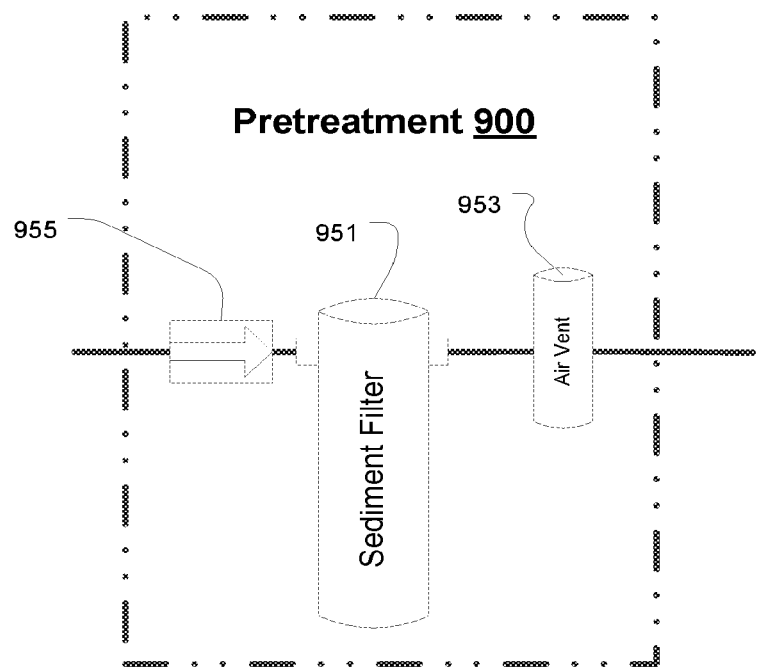
FIGS. 6, 7, and 8A illustrate portions of an embodiment of a fluid preparation apparatus.

Referring to FIG. 6, pretreatment module 900 is shown in more detail. A check valve 955 prevents backflow. An air vent 953 removes air from the primary supply and a sediment filter 951 (which may be replaceable) provides substantial filtering of solids.

Figure 7:
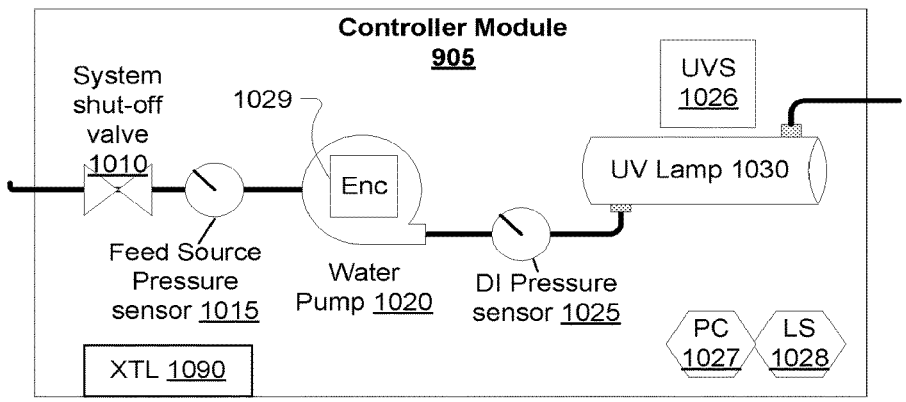

Referring to FIG. 7, the control module 905 is shown in greater detail. A shutoff valve 1010 is provided for safety. Pressure indicators 1015 and 1025 may be provided for monitoring the respective pressures in and out of a pump 1020. Feedback regulation may be provided to ensure that consistent metering is provided if the pump is relied upon for measuring the total quantity of water supplied to the batch container 1. A high intensity ultraviolet (UV) lamp 1031 provides a both sterilization mechanism and a mechanism for removing chlorine and chloramines. Preferably, the UV lamp 1030 is of such intensity and wavelength as to provide disintegration of chloramines. In a preferred embodiment, the lamp is characterized by a 245 nm wavelength and an output power of 750 m J/cm$^2$ up to 1500 m J/cm$^2$ which is sufficient to remove chloramines. By oxidizing chloramines and subsequently, as described below, filtering using a deionizing filter, chloramines can be removed.

Note that pressure indicators 1015 and 1025 may be pressure transducers that feed control signals to a control device such as discussed with reference to FIG. 1 B and to be discussed with reference to FIGS. 13A and 13B. The operation of pump 1020 may be controlled in dependence on pressure indications from such transducers. For example, if a high head pressure is indicated, an alarm may be indicated and the pump shut down. This may indicate a problem with a connected filter. Also, the pump may be operated for a short interval and a pressure decay profile recorded and compared with an expected decay profile. If the profile does not match, it could be used to indicate a leak (such as in a filter or line) or a clog in the system. If the upstream pressure goes low, it could mean that the water supply is turned off or some other fault. Each of these events may be indicated by means of an annunciator or display (e.g., see 330 and 380 at FIGS. 13A and 13B and attending discussion) and/or by switching off the pump to avoid damage to the system and to notify the operator to take corrective action.

Figure 8A:
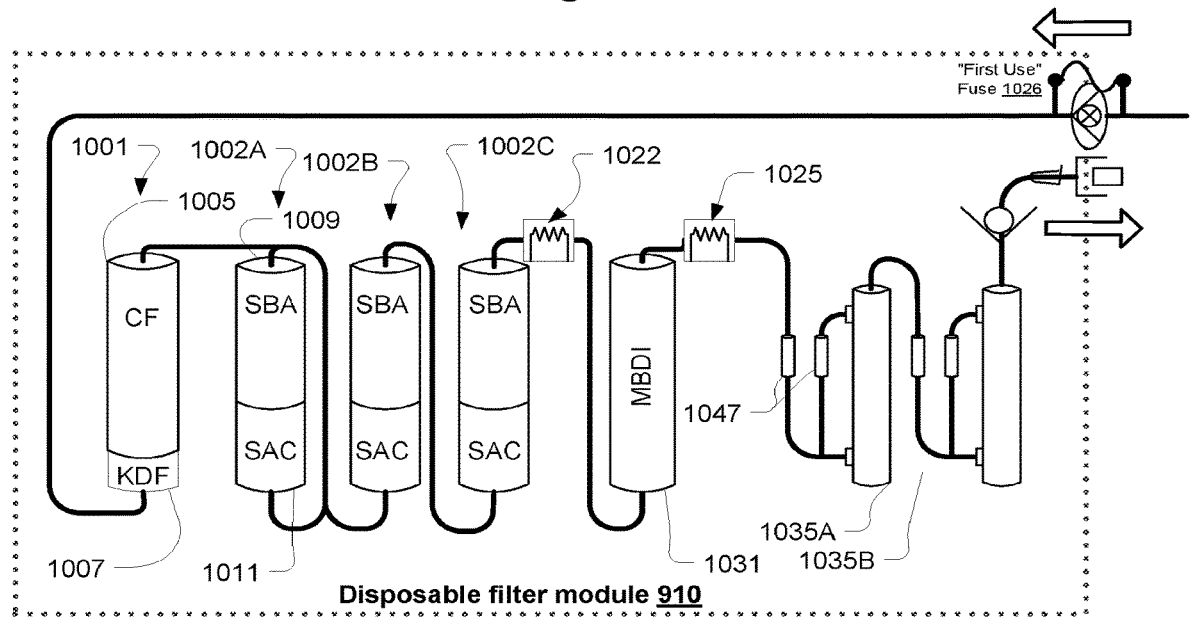

Referring to FIG. 8A, the replaceable (disposable or remanufacturable) filter module 910 contains a first stage filter 1007 copper-zinc alloy which is used to subject the water to a reduction/oxidation process to remove ions. This removes ions through a chemical reaction. An embodiment is KDF 85 media where about one pound is used for a flow rate of 150 ml./min water flow rate. A activated carbon filter 1005 follows which is a well-known adsorption type filter. Next three stages of strong acid cation (SAC) 1011 and strong base anion (SBA) 1009 filters follow in series. The SAC/SBA filter cartridges 1011/1009 are not mixed beds as typically used in water filtration applications. They separate the cation and anion stages as illustrated because it has been determined to be much more effective at removing colloidal aluminum from the treated water. Note that the order of the SCA and SBA beds is not limited to what is shown and that they can be housed in a single canister or multiple canisters. Also note that other components can be sequenced differently as well as should be clear from this disclosure. For example, it should be clear that the pump 1020 can be used in a pushing arrangement to draw water through the UV lamp and the particulars of the arrangement are not limiting to the inventions disclosed. Also note that the resistivity probe 1022 can be included within a single deionizing filter between previous and following deionization stages and employed to similar effect. In such an embodiment, a deionizing filter would have leads or contacts to connect the probe to an external measurement device or controller.

Note that instead of using layered beds in a single cartridge as described, separate cartridges each containing one of a SBA and SAC filter bed may be used. Also, each cartridge could contain more than one layer of each to provide similar results.

The resistivity probe 1022 detects ion concentration by contact testing of the resistivity of the water. A signal is generated to indicate that this will be the last allowed batch before the system will require the replacement of the replaceable module 910. Control may be provided as in the embodiment of FIG. 1B, discussed above. The second filter in the present embodiment, which backs up the first stage suffering from breakthrough, is a mixed bed deionization filter 1031. This ensures that the current batch can be completed. A second, final safeguard resistivity or conductivity test is provided with an audible alarm at 1025 as a back up safety measure. If the value it detects is above a certain level, the pump 1020 may be shut off and an alarm sounded. This may come into play if the resistivity probe 1022 fails, or if the safeguards discussed with reference to FIG. 1 B are breached. TP is a hydrophobic membrane air vent which allows air in ultrafilters 1035A and 1035B to be purged. The ultrafilters 1035A and 1035B may be a microtubular filter such as used for dialysis. An air vent may also be provided as shown at 1047. The air vent may, for example, have a 1.2 micron hydrophilic membrane that blocks air. There is a hydrophobic membrane port which allows air to vent from the filter. These are available as off the shelf components. Any suitable air elimination device may be used and these features are non-limiting of the described embodiments. Also, the second stage MBDI type filter 1031 can be a layered deionization filter such as 1002C with the same benefits as described in terms of providing protection against breakthrough. Also, the final resistivity sensor 1025 can be located as shown or moved to another location downstream of the final deionization stage, such as after or between the ultrafilters 1035A and 1035B, and the configuration shown is not limiting of the invention.

Note, it should be clear that resistivity probe 1022 may be used in a configuration such as that of FIG. 1 B, with the resistivity probe 1022 corresponding to sensor 405 such that filter module 910 corresponds to filter module 425.

A simple device for enforcing against re-use or use of an expired device is to employ a fuse that the system burns out when a component is first used. For example, the disposable filter module 910 described with reference to FIG. 8A may be fitted with a fuse 1026 that is burned out when first connected to the controller module. The condition of the fuse can be detected if the same module is later connected to the controller and the controller may the prevent its re-use. In a broad sense, such a fuse embodiment may be considered a type of data carrier whose state is changed to indicate a first use. The same device may be used when the module is determined to have been expired, for example if a contaminant break-through is detected by resistivity sensor 1022. Thereafter, the disposable filter module 910 may be prevented by the controller from being used after an attempt to reconnect by burning out a fuse or updating a data carrier to indicate the break-through ("expired") status.

Note that two separately-housed ultrafilters 1035A and 1035B are serially interconnected. The separate housings ensure against failure mechanisms such as grow-through of pathogens, adjacent simultaneous or shared seal failure. For example, prior art reference US Patent Publication No. 2003/0105435, cited in the Background section, shows a filter cartridge with two microporous membranes in adjacent layers of a filter cartridge housing. These may share a seal mechanism or adjacent seals such that failure of the seal of one necessarily involves failure of the seal of the other. Also once a grow through problem occurs in one, the adjacency may cause the problem to creep directly into the adjacent membrane. These problems are prevented by the illustrated arrangement of separate redundant ultrafilters.

Figure 8B:
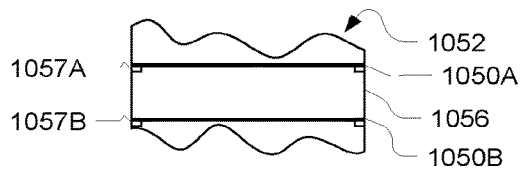
FIG. 8B illustrates a portion of a filter module in which two redundant ultrafiltration membranes are commonly housed.

Note that the benefit of separately housed filters may be substantially provided in a single housing by substantially separating two ultrafilter layers. Referring to FIG. 8B, for example, a multilayer filter with various types of filter elements housed in a common cartridge 1052 contains two ultrafilter layers 1050A and 1050B. The two ultrafilter layers 1050A and 1050B, separate membranes, are kept apart my an intermediate layer 1056, which may be a spacer or another filter medium. Separate seals 1057A and 1057B, which are also spaced apart, are provided.

Note the final conductivity/resistivity sensor/alarm 1025 may control the pump, as noted. A controller 1090 may be connectable to the disposable filter module 910 and configured to stop the pump 1020. The trigger resistivity safety level to cut-off the pump 1020 may be 1 megohm, but may be raised to 2 megohm to allow the use of required temperature compensated resistivity probes (an FDA & AAMI requirement) This does allow use of low cost in-line resistivity probes in the disposable filter module 910.

Preferably, the filter module 910 as well as the modules of other embodiments are of such a flow rate that upward flow of fluids is possible. Generally, prior art deionization beds suffer from the problem of floating or loosening resin particles which may have been disturbed during handling. The separation and floating of the particles breaks up the beds and renders the filters less effective. To avoid this, generally, filter systems are configured to direct flow downwardly through the beds to help keep and compress the resin particles. But if flow rates are kept low, as may be done in the present system, water may be flowed in an upward direction which helps to eliminate air from stream. Air is a notorious problem in the preparation of medicaments such as dialysate. The precise flow rates needed to allow upward flow will vary according to the characteristics of the system. One way to allow faster flow rates without being hampered by break away resin particles is to provide a bed compressor of resilient porous material to compress the bed. Referring momentarily to FIG. 12, 5 in a filter cartridge 1 150, a resilient compression layer 1140 urges the filtration material 1145 in a downward direction. The resilient compression layer may be any suitable polymeric or rubberlike material that is compatible with the application.

The following is an example procedure for using the devices discussed with reference to FIG. 4.

1. Remove the dialysate concentrate tubing set 915 and remove the cap 14 from the tubing line 7 that contains the filter 11. (The 0.22 micron filter 11 provides additional protection from inadvertent contamination.)
2. Connect the outlet line 404 to the concentrate bag luer 5 connection 9.
3. Break the frangible luer connector 4 which connector is configured to form a permanent seal on the side facing the Y-junction 5 when disconnected.
4. Add predetermined quantity of water into the concentrate bag using the purification plant through tubing branch 7 through luer connector 9.

5. Optionally a user can write on the bag label the date and time water was first added to the concentrate bag, to assist in ensuring that it is used within a period of time. An automated scheme may be employed as well.
6. Shake the batch container 1 well to mix.
7. Confirm solution conductivity prior to use. Remove the break-off cap 1 and draw sample from this branch 15. After removing the sample, clamp the line using the pinch clamp 17 provided.
8. (The following is normative according to a preferred embodiment and not limiting of the invention) Conductivity must be in the range 13.0 to 14.4 mS/cm. Nominal conductivity for the dialysate solution is 13.7 mS/cm at 25° C. If conductivity does not meet this specification do not use it. Verify that the results are accurate. If conductivity is high additional water may be added to bring it within specification. If conductivity is low then the solution must be discarded.
9. Using the non re-opening clamp 13 provided, clamp the line that is connected to the water purification plant.
10. The clamp 6 is, next, clamped on the line that is connected to the dialysate bag 1.
11. Disconnect the water source at the luer connection 26.
12. Connect the bag of dialysate solution to the dialysis circuit at the connection 8. This leaves the filter 11 and permanent clamp 13 in place to protect the water supply source.
13. Unclamp the line going to the dialysate bag using clamp 6, and initiate treatment after verifying that dialysate will be used within 24 hours from when water was added.

Figure 9A:
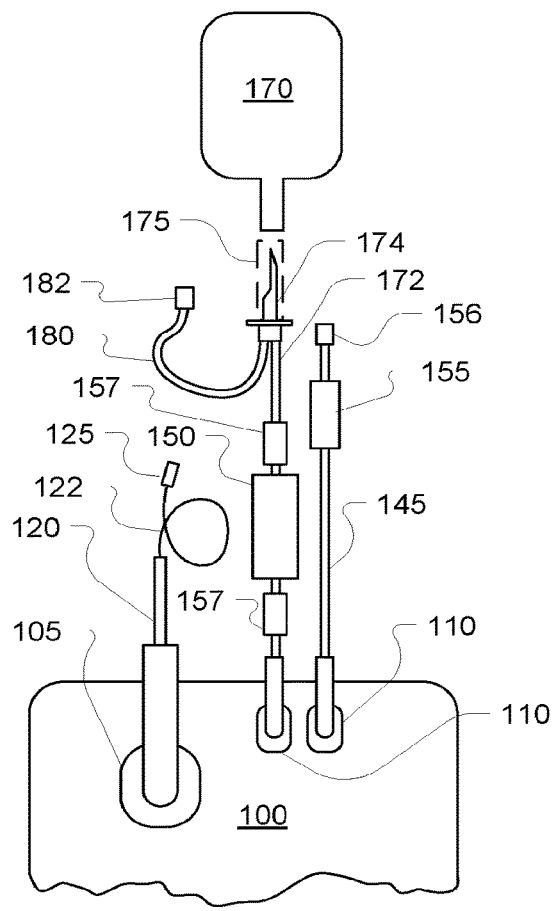
FIGS. 9A and 9B illustrate embodiments of a batch container.
Figure 10A:
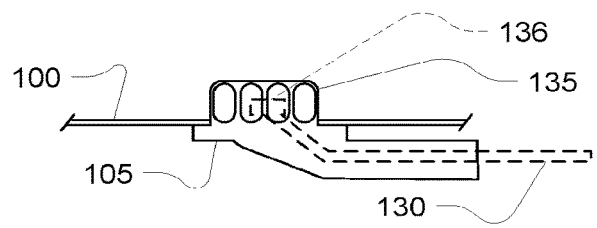
FIG. 10A illustrates a fluid quality sensor such as a conductivity or resistivity sensor configuration for sensing fluid quality in a container.

Referring to FIGS. 9A and 10A, a batch container 100 has a fluid quality sensor 135 of a probe 120, such as a contact-type conductivity sensor. The latter may simply be two metallic surfaces separated by a known distance and of a given area that has been calibrated. A cage 136 in a support 105 sealed to the wall 130 of the batch container 100 which may be a polymer bag as typically used in the medical industry. The cage 136 prevents an opposing wall (not shown separately) from preventing fluid from circulating around and through the cage and in contact with the probe such that a reading of the probe 120 is improved. The probe 120 extends from the support 105 and has a lead 122 with a signal connector 125 that can be connected to a controller (discussed later). The probe 120 is an independent element and can be used with any of the embodiments so its description here in combination with other features is not intended to be limiting. Note that preferably, the probe assembly is permanently sealed to the batch container such that there is no possibility that contaminants can enter the batch container 100 interior.

At 110, a fitting connecting a sample or feed line 145 is shown. The latter may be used, with a connector 156, connect a sampling syringe to draw out a sample of a medicament or infusate. A check valve may be provided at 155 to prevent ingress of contaminants. A clamp (not shown separately) may be provided as well to guard against contamination. In an alternative embodiment, line 145 may be configured for injecting a soluble concentrate into the batch container 100 before the container 100 is sealed and sterilized as a unit (for example, by gamma ray sterilization). When a prescribed quantity of purified water is added to the batch container, the diluted concentrate may form a medicament or infusate such as replacement fluid for hemofiltration or a dialysate for hemodialysis. Line 145 may also represent a draw line that may be connected to a treatment machine. In the latter case, a sterile filter (at 155), such as a microporous membrane of 0.2μ may be provided to guard against touch contamination. Additionally, a clamp may be provided as at 155.

In the embodiment of FIG. 9A, purified water may be added to the batch container by another instance of a line similar to 145. Alternatively, if concentrate or other medical solute or medication is contained in a separate container, such may be added to the batch container 100 by means of a double lumen spike 174. (Details of a suitable dual lumen spike can be found in US Patent Publication No. 2004/0222139, which is hereby incorporated by reference as if set for in its entirety herein). A spikable bag 170 contains, for example, medical fluid concentrate such as concentrated dialysate. Purified water is pumped through connector 182 of line 180 and passed into the bag (after spiking) by the dual lumen spike 174. The fluid circulates in the bag carrying its contents back through the dual lumen spike 174 through line 172, through a filter 150 into the batch container. The dual lumen spike may be sealed by means of a removable cap 175 so that the batch container and fluid lines can be sealed and sterilized and later delivered as a unit without contamination. Clamps 157 may be provided to seal the batch container 100. A special clamping connector 442 may be provided and used as discussed with reference to FIG. 1 B in line 180. If concentrate is present in the batch container 100 rather than using a spiking bag 170, the concentrate may be used to obtain a data point for a calibration line fit for measuring fluid conductivity.

Figure 9B:
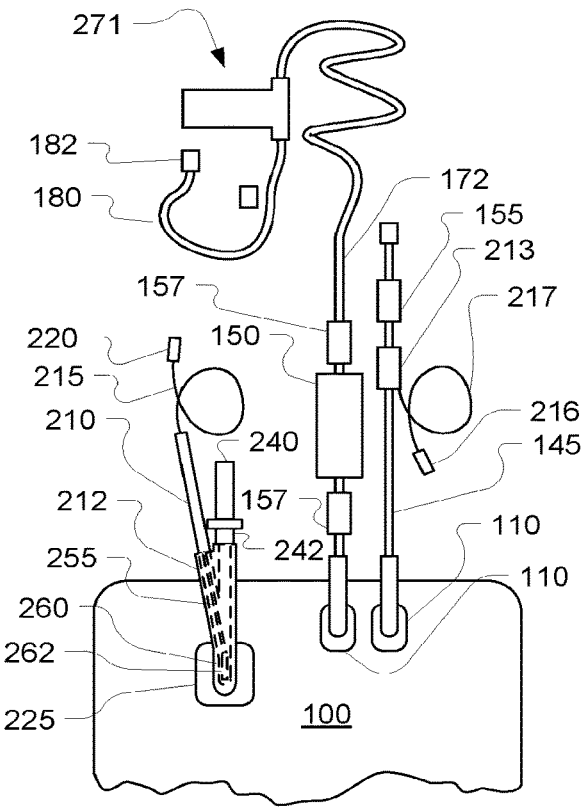

Referring to FIG. 9B, instead of providing a conductivity or resistivity sensor in the batch container 100, a dual lumen takeoff 255 with a common lumen (Y-configuration) 260 housing a water quality sensor 262 of a probe 210 with corresponding signal connector 220 and lead 215. A syringe port 240 and check valve 242 are connected inline to the other branch of the Y-junction. When a syringe (not shown) is attached and fluid drawn into it, fluid from the batch container passes over the water quality sensor to allow its quality to be measured. In other respects the elements of FIG. 9B are the same (and identically numbered) as those in FIG. 9A.

Referring to FIG. 11, a replaceable multiple use filter module 1125 as may be used in the various embodiments described herein has an inlet port 1130 and an outlet port 1110. A physical arrangement of filter cartridges 1111 is shown which provides for a compact module 1125 that is advantageous for packaging and assembling to a chassis (as discussed relative to FIGS. 13A and 13B). Tubing 1116 runs from the top of each cartridge 1111 to the bottom to provide upward flow as discussed earlier. A signal port 1100 for reading fluid quality sensors 1115 and 1105 is provided in a housing 1127. Signal port 1100 may have a lead wire and connector installed to it or one may be provided separately. Alternatively, signal port 1100 may be a wireless port powered by a battery. Signal port 1100 may include a data carrier as discussed with reference to FIG. 1B or a data carrier may be provided separately or without the signal port if a fluid quality sensor is not provided.

A data carrier may include software and instructions for using the filter module 1125. These may be read by a permanent component of a filtering system as described in connection with FIGS. 13A and 13B. A base unit 335 may be configured substantially as described with reference to FIG. 5 with the base unit 335 housing the components of the permanent pretreatment module 900 and controller module 905. The base unit may contain a display 330, such as an LCD display. Instead of, or in addition to, a display, the base unit (and other embodiments described herein) may have a voice generator or other type of output device. An inlet port 341 may be provided for receiving raw water to be filtered and an outlet port 340 for attachment to a filter module (which may be multi- or single-use) which is received in a locating station 315. The latter may have a reader 311 to read a data carrier or to connect with a fluid quality probe such as one or more conductivity sensors described above. A further locating station may be provided such as 305 for a batch container. This may have a data carrier reader 320 and/or various other components (at 321) such as a heater, a mixer, such as a moving field generator for magnetohydrodynamic mixing of the contents of an installed batch container. The base unit 335 may have a port 310 for connection to a fluid quality probe of the batch container. This may provide a calibration input as well as a final measurement of fluid quality. The embodiment of FIG. 13B additionally provides a locating station for a concentrate container such as 170 described with reference to FIGS. 9A and 9B. The base unit 335 may further be fitted with a controller containing a computer with a connection to the Internet or other network connecting the base unit with a server 390.

In an embodiment, features indicated at 301-306 may be added to allow the base unit 335 to control when and whether an outlet line of a batch container should be opened and clamped. A batch container is fitted in the station 305 and an outlet line of the batch container fitted between clamping portions 303 and 304. A detector 306 verifies that the line has been fitted in place. When the system is run, an actuator 302 and motor 301 may be activated to clamp the line during fluid purification and as the batch container is filled. After the batch is filled, the clamp may remain closed until a treatment operation, which may be run while the batch container remains in place, is begun. At treatment time, the clamp mechanism 303 and 304 can enforce the expiration time of the batch of fluid. For example, a timer can be started within the controller of the base unit or, equivalently, a time/date stamp stored and the clamp only released if the batch of fluid is used for treatment within a certain period of time. For this purpose a treatment machine and the base unit 335 may be combined into a single device under common control or the two may be linked by a data link to operate cooperatively to achieve such a result. The flow chart of FIG. 15 describes the control steps involved.

Figure 10B:
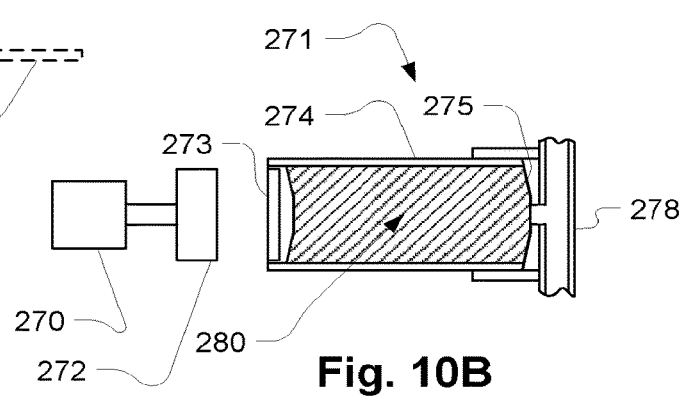
FIG. 10B illustrates a medicament concentrate cartridge.

Referring now to FIGS. 9A and 10B, instead of a concentrate container in the form a spikable bag 170 as illustrated in connection with FIGS. 9A and 9B, a cartridge 271 as illustrated in FIG. 10B may be used. Here, concentrate 280 is within a sealed cylinder 274 with a piston 273 and a burstable seal membrane 275. The cartridge may be fitted in the base unit 335 (FIGS. 13A and 13B) which may contain a linear drive 270 and plunger 272 to push the piston 273 thereby bursting the seal membrane 275 and inject contents into a T-junction 278 in the path of purified water sent into the batch container 100. Note that the cartridge 271 may be provided as part of the sterile batch container fluid circuit shown in FIG. 9B.

Figure 15:
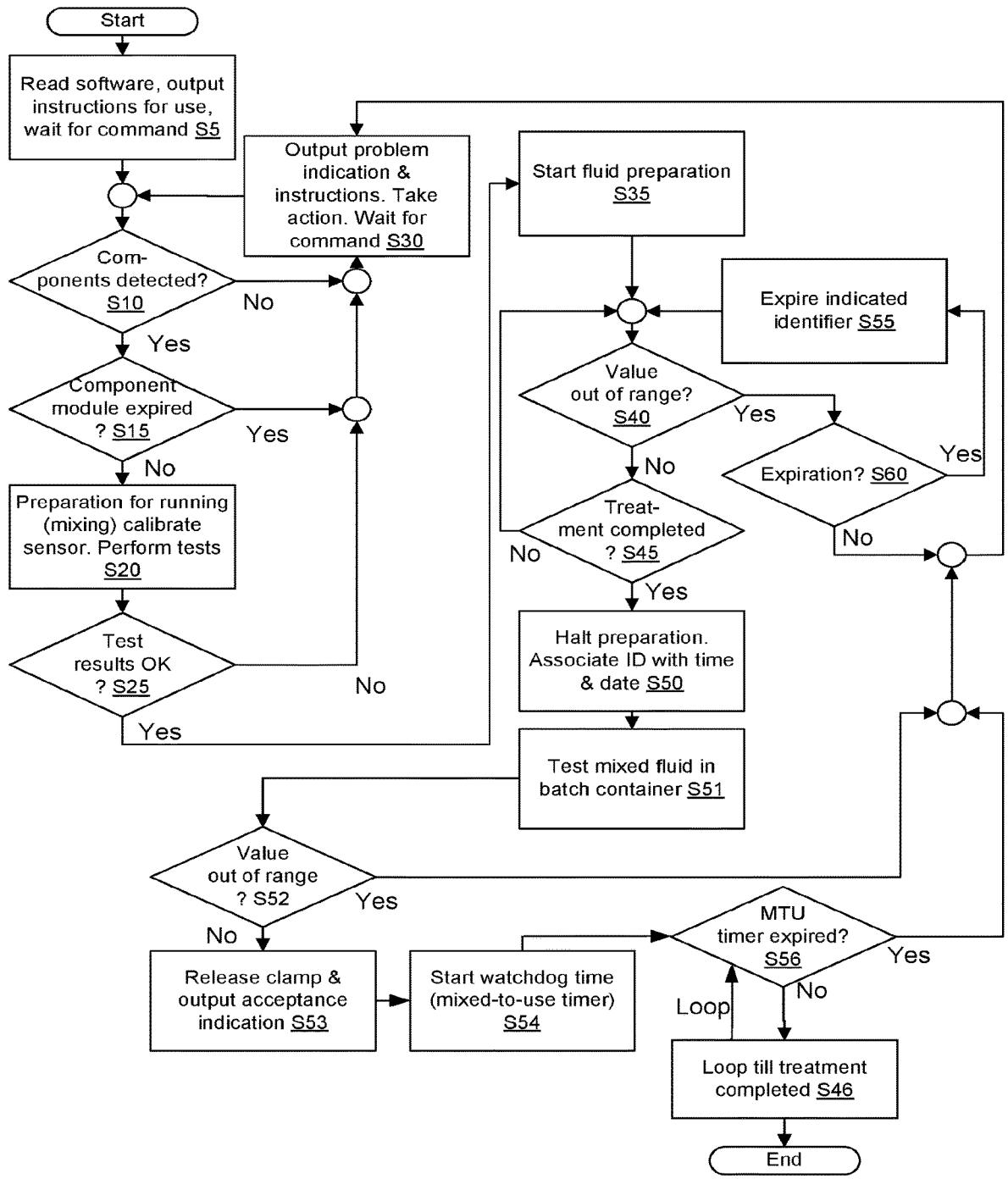
FIG. 15 is a flow chart for discussing various control options of the various embodiments discussed herein.

Referring to FIGS. 14 and 15, the base unit 335 and corresponding parts of other embodiments described herein, may contain a programmable controller including an embedded computer 600 with memory, non-volatile storage, communication elements, etc. Various sensors 605 such as discussed in connection with various embodiments may be connected to provide input to the controller executing a program stored in memory. The latter may stored in firmware or obtained from a data carrier via a data port 610 as described previously. In addition, a network or Internet connection to a server 625 may be provided to obtain and transmit data such as software, instructions for use, expired identification codes, etc. Actuators 615 such as valve clamps, pumps, and annunciators 620 such as alarms may be provided as well.

A sample program for operating the various embodiments described herein is shown in FIG. 15. The process may begin with firmware until software loaded at a later stage takes over. Software may be read from a data port or data store and instructions for using the system output at step S5 whereupon the system waits for user input. The instructions may indicate to press hard or soft key to continue at which point steps S10 and S15 are executed to determine if a no-go condition exists. If a necessary component (S 10) has not been connected, step S30 will be executed and the system may output an appropriate message to instruct the user to take corrective action and wait for response. Similarly, if in step S15, it is determined that a component is expired, such as a batch bag that has been previously used or a filter module has been used and previously indicated as having suffered breakthrough, step S30 will be executed. At step S20, various system tests may be performed such as a pressure profile test or quality test. Tests may also include determining if the conductivity indicated by a connected conductivity probe is within specified limits. In step S25 it is determined if all tests have been passed and control passes to step S35 where fluid preparation is begun. If not, step S 30 is performed and appropriate output is generated on a display such as 330. If a value goes out of range at step S40, control passes to step S60 to determine if an expiration event has occurred, for example, breakthrough of contaminants in a filter module. Note that Filter modules may be "stamped" with a permitted time of use after a first use when presumably the seal was first broken. This may be enforced in the same manner as discussed with reference to attempted reuse of a filter module after breakthrough was detected. Thus, step such an event may be detected at step S60 as well.

At step S55 depending on the type of data carrier (e.g., programmable or just carrying a unique ID), the expired or spent unit is indicated as expired so that reuse can be prevented. For example, in S55 the data carrier may be programmed with a token to indicate that the attached filter module is expired or a server may be sent a message to indicate that its unique ID should be added to a list of expired IDs. Any suitable device may be used to "expire" a unit. Since expiring a unit may still allow a batch to be prepared, control returns to S40. Completion of the treatment may be determined at step S45 by measuring the total mass pumped or by other means. For example, if the embodiment provides a conductivity probe in the batch container, step S45 may depend on the measured conductivity of the batch contents. Once completion is determined, the system may be halted at step S50 and the batch bag "stamped" with a time and date. Note that further instructions may be output at this point.

In one embodiment, the water purification and treatment may be done from a single apparatus and under common control. The steps following step S50 illustrate this. Assuming purified fluid has been added to a batch container of some description such as those described in the current specification or some other, the contents of the container may be mixed, if a solute is involved, and the contents checked in some way in step S51. For example, the conductivity of a mixed batch or the resistivity of a pure batch can be checked determine its conformity with treatment specifications. In step S52, if a value is out of range, control passes to step S30, but if not, the batch may be utilized at any time up to an expiration time/date (MTU time, or Mixed Till Use-time). In step S53, an outlet clamp that prevents fluid from being drawn from the batch container is released to allow a treatment to be performed with the fluid product. At the same time, an acceptance message can be output to the user on a display. At this time, in S54, a time stamp is stored or a timer started to keep track of the expiration of the batch of fluid. If the expiration is not observed, which is tested at step S56 by checking to see if the timer has expired, the clamp will close in step S30 (under the general step indicated as "take action") and an appropriate message output. The system will then wait until treatment is completed while, optionally, continuously checking the MTU timer in steps S46 and S56.

Note that many of the described mechanical and control features are novel and inventive alone, as subcombinations with other features and their description in combination in the above embodiments is not intended to be interpreted as limiting of the inventions disclosed herein. Referring to FIG. 16, when a treatment machine 700 attempts to use a batch container 710 tagged with an expiration date at step S50, it can determine if the date has passed and prevent use of an expired batch container thereafter. This may be implemented with contact or wireless data reading devices, a programmed smart card type device or via an Internet server as described with reference to the mechanism for enforcing non-reuse of filter modules.

Referring to FIG. 17, air may evolve from fluid as it passes through an ultrafilter 714. Preferably, the ultrafilter 714 has a high membrane surface and in such filters, the potential for air evolution may be fairly high. To avoid problems with bubbles forming in the filter, the embodiment of FIG. 8A shows transducer protectors TP, which are hydrophobic air vents. But the lines leading to them can fill with water and render them useless for air purging. A refinement of the configuration of FIG. 8A, which may be used in any water treatment plant as a final protective stage, is to provide an ultrafilter 714 (which may be a standard dialyzer capped at the lower blood port) with an inlet 712 and outlet 704 on one side of the membrane connected by a return line 704 flowing through an air filter/vent 706, through further line 708 into a T-junction 717 and back into the inlet line 712. Ultrafiltered fluid is drawn out through line 707. Again, the filter/vent 706 may be a 1.2 micron air vent with a 1.2 micron hydrophilic membrane that blocks air and a hydrophobic membrane port which allows air to vent from the filter. These are available as off the shelf components. The water column defined by line 708 is denser than the corresponding column within the housing of ultrafilter 714 so that a return flow will exist through the branch 704, 706, 708. The reason for the lower density is due to the evolution of air in the ultrafilter 714.

An alternative design that integrates air vent configurations into the housing of the ultrafilter 714 is shown in FIG. 17A. For the outlet (filtrate) side of the media, an air vent, e.g., a hydrophobic membrane type air vent 765 may be integrated into the outlet of an ultrafilter 715 and an air filter such as a hydrophilic air filter membrane 766 integrated into the outlet. Any bubbles coming out of fluid collect at the top of the filtrate side (in a header space of a microtubular membrane type filter) and be vented by the hydrophobic air vent 765. On the inlet side of the ultrafilter 715 (the side of the filter media that has not yet been ultrafiltered), air collecting in the inlet side will leave by an air vent 467, for example one using a hydrophobic membrane 469. A check valve 742 may be provided to prevent siphoning and/or reduce risk of contamination.

Referring to FIG. 18, to address any problem with inadequate flow through the return branch of the FIG. 17 embodiment, a resilient channel element 730 such as an inline bladder 731 may be included with check valves 724 and 728. When the system pumps fluid, the resilient channel element 730 stores fluid under pressure and releases it in pumping fashion when the system stops pumping. Again, an air filter/vent 724 allows air to escape and purged from the return line 726. The return flow problem can also be dealt with by replacing the T-junction 717 with a Venturi device configured to create a suction in line 708 by using an accelerated fluid flow through the line 714,712.

One of the drivers for the features discussed above is a need to provide pure water irrespective of input water quality. The above embodiments are not reliant upon water quality and are designed to reliably produce pure water or solutions regardless of input water quality. Various embodiments are also designed to reduce the costs associated with lower volume (10-60 liters) preparation of medical and other pure solutions and to maintain simplicity through the combination of semi-permanent and single-use modules which combine to eliminate the complexities, costs and safety issues associated with maintenance, sterilization, and operation of many other prior art systems.

In the following sections, systems are described which is configured to prepare batches of medical fluid, such as dialysate for dialysis or replacement fluid for hemofiltration. The systems according to exemplary embodiments produce and store a single batch that contains enough fluid for multiple treatments. In a preferred embodiment, the fluid is prepared such that it has a very low rate of endotoxins and contains solutes that are compatible with storage for multiple days, such as lactate-based dialysate. The embodiment purifies water, dilutes a lactate based dialysate concentrate to form a batch, for example of 80 l. volume. The batch is stored for a specified period of time and used for frequent low-volume treatments, for example, three daily treatments. The system provides safety systems that enforce adherence to storage term constraints, purity, fluid and quality. In addition, the system strikes a unique balance between the risks long-term storage of medicaments while keeping available for immediate use, treatment frequency, volume of fluid, portability of the storage unit, and other factors to provide an overall positive impact on patient lifestyle and well-being. The features, in combination, include:

1. Frequent treatment with moderate clearance (e.g., daily) may be selected as a treatment regimen according to one preferred embodiment although this is not required;
2. Preparation of treatment fluid every several days (e.g., every three days);
3. Storage at a temperature that allows immediate fluid withdraw for treatment purposes between fluid preparation steps;
4. 1 and 2 can be accomplished with fluid volumes of 80 l. or so, for example. Such a quantity, which may also correspond to other treatment types, is a convenient quantity for a portable unit such as one that can used at a residence.
5. A consequence of 2 is that the task of preparing fluid can be done at times other than treatment times (i.e., out of synch with treatments) thereby permitting a patient's schedule to be more flexible and also reducing the length of time spent performing the treatments because the preparation does not have to be done as part of any of the treatments.

6. Enabling the generating purified fluid at a patient's residence or other convenient treatment site avoids storage requirements.
7. Employing water purification based on deionization (DI) and storage at usable temperatures, combined with the high treatment-frequency and moderate clearance can reduce the demands on utility infrastructure, namely water and electrical, because the high power rates for fluid heating and high water rates associated with reverse osmosis are avoided. In other kinds of systems, high power rates are often required for sanitization of the water treatment system. DI and ultrafiltration provides a prolonged use disposable that does not require sanitization. Water usage is reduced through the use of deionization vs. RO, since this DI does not have a "waste stream".
8. The batch size permits a unitary design and, with compact packaging, may be made no higher than a household side table or no higher than about a meter and preferably no higher than about 75 cm, or the height of a typical table. In a preferred embodiment, the height is about that of a lamp or end table or about 65 cm.
9. An attractive enclosure that hides components permits an unintimidating and attractive appearance to be maintained if the treatment site is a residence.
10. The small size permits the enclosure to be made mobile and so the enclosure may be fitted with wheels.
11. A tabletop may be provided on the enclosure to allow different types of treatment equipment to be supported by it. Preferably, in keeping with the appearance objectives, the tabletop is not interrupted by protrusions such as poles, displays, and other fixtures.
12. 11, along with appropriate mechanical design features the allow the unit to output the stored fluid at a pressure similar to the normal medical fluid bags used for typical medical treatments, may permit convenient switching from a peritoneal dialysis (PD) cycler unit, until a patient's peritoneum cannot handle PD to extracorporeal blood processing simply be replacing the PD cycler with an extracorporeal device.
13. The size range for the batch container and an appropriate support mechanism and leak detection may enable the use of a disposable container to simplify preparation of the batch.
14. Filtration using deionization beds, particularly with a large safety margin, can be expensive so a long term multi-use disposable component may provide a cost balance point while also making it convenient for users because of the need to replace, for example, only once every month or even less frequently. In a preferred embodiment, the module is replaced once every 1-3 months.
15. Multi-day, multi-treatment storage, is enabled by using a lactate based treatment fluid and a pre-sterilized, disposable container with a preconnected sterile filter that treats all fluid entering the sterile, disposable storage container.

Figure 19A:
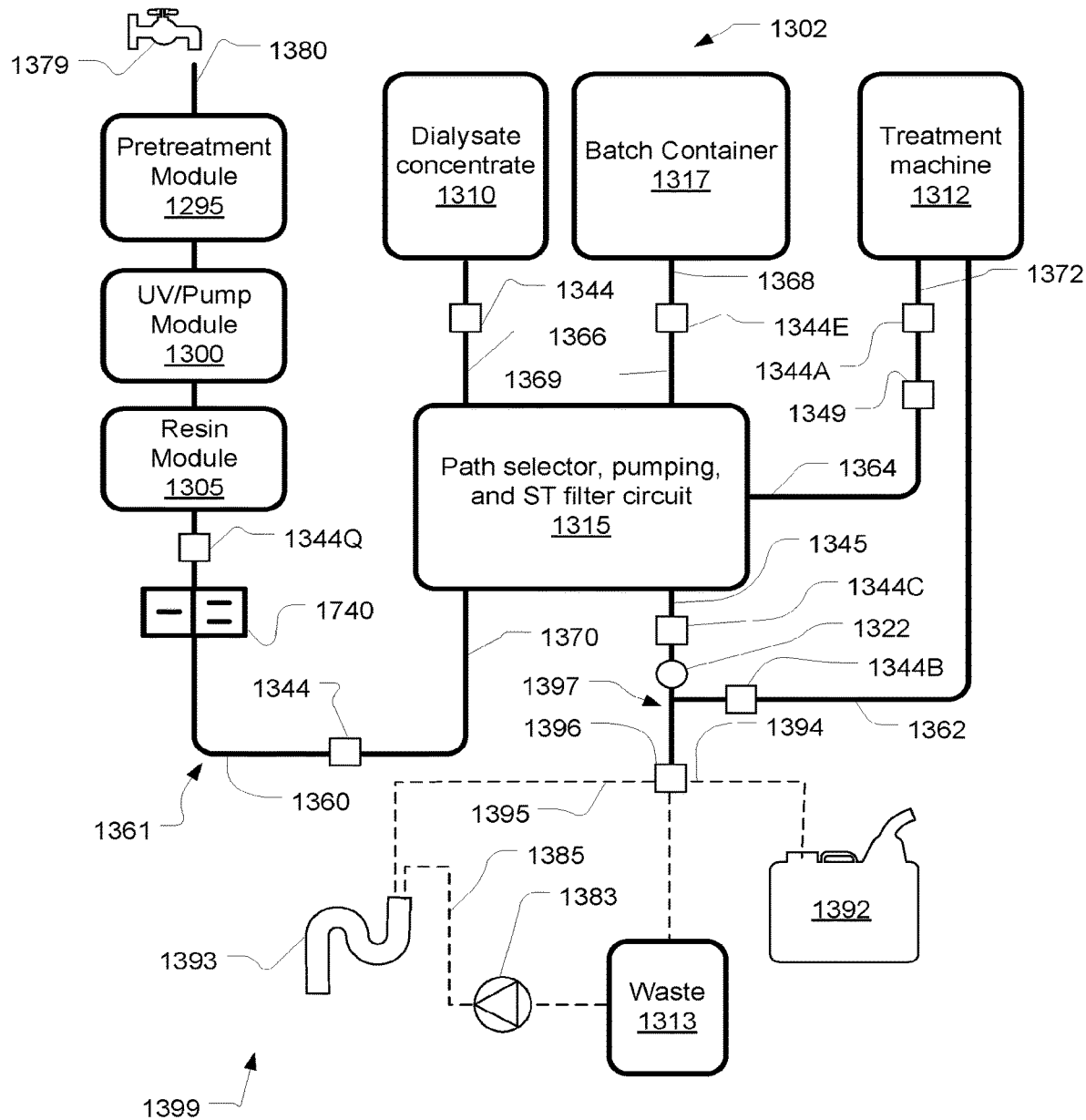
FIG. 19A is a flow diagram of a treatment fluid preparation and storage device according to an embodiment of the invention.

Referring to FIG. 19A, a preferred configuration of such a fluid preparation and storage 1302 system is shown. A pretreatment module 195 receives water from a source, such as a sink faucet 1379, and a UV/pump module 1300 may provide a semi-permanent pre-filtration process as described with reference to FIGS. 6 and 7. The water quantity requirements are preferably such that ordinary household supplies are adequate—as will be observed, the preferred embodiments described permit this. The connection to a sink faucet may be by way of a common connector that replaces the aerators of many household faucets. A long term filter (LTF) module, for example, 1305 provides water purification for multiple multi-treatment batches, for example sufficient for daily treatments for 30 days. In a preferred embodiment, the LTF module 1305 includes KDF, segregated SAC/SCA bed deionization (DI), and mixed bed and ultrafiltration as described with reference to FIGS. 2A and 8A. The LTF module, as also described above, may be in the form of a completely disposable module which only requires a small number of connections to replace. Various connectors are shown at 1344.

A disposable circuit 1303 includes a batch bag 1317, and various fluid circuit elements. Beginning with the connector 1344 for connecting to the LTF module 1305, a dongle 1361 has of a tubing segment 1360 with respective connectors 1344 and a non-reopening clamp which is pre-installed and continuous with a feed line 1370. The dongle 1360 may be as described with reference to FIGS. 2A and/or 3, for example. The disposable circuit also includes a path selector, pumping, and short term filter portion 1315. An embodiment of the latter is described with reference to FIG. 23, infra. The latter contains a short term filter (not shown here) that is used once for each batch of treatment fluid prepared. A line 1366 may be provided for connection to containers of medicament concentrate 1310. Another line 1368 may connect a pre-connected and sealed batch container 1317 for storing sufficient medicament for multiple treatments to a line 1369 via a connector 1344E. Note that the connector 1344E may or may not be provided between the batch container 1317 and the path selector, pumping, and ST filter circuit 1315 since they may be supplied as a single presterilized disposable.

A source line 1364 may be provided to provide water to a treatment device 1312 such as a hemofiltration machine or peritoneal dialysis cycler. The treatment machine 1312 may include a fluid circuit (not shown separately) which includes a connector 1344A for a source line 1372 and a drain line 1362 with a connector 1344B. The may be connector to mating connectors on a panel (not shown here) of the fluid preparation and storage system 1303. Connectors 1334B and 1344C of the fluid preparation and storage system 1303 may connect at a Y-junction 1397 to provide a single common drain connection 1396 which may be connected to a sewage service 1393 or to a spent-fluid container 1392. In yet another embodiment, the fluid preparation and storage system 1303 may provide a disposable waste container 1313, waste line 1385, and a pump 1383 to collect and discharge waste fluid after each treatment or when a new batch is prepared (the procedure for which will be described shortly). The collection of waste in a container is not required in the fluid preparation and storage system 1303 but in some cases it may be preferred, such as when long term connection to a drain 1393 is not convenient or when a patient wishes to move the treatment 5 location frequently. A fluid quality sensor 1322 such as a conductivity sensor, opacity sensor, bubble detector; is provided in a discharge line 1345 to allow the treatment fluid to be tested for quality by sending a sample through the discharge line 1345. The fluid quality sensor 1322 may be rinsed in a further step by pumping purified water through the discharge line 1345.

Figure 19B:
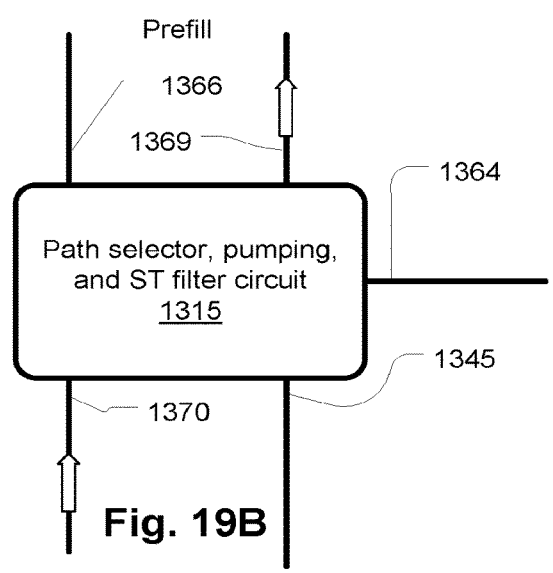
FIGS. 19B through 19H and 19J illustrate operating modes of a flow circuit component and control component of a treatment fluid preparation and storage device according to an embodiment of the invention.
Figure 19C:
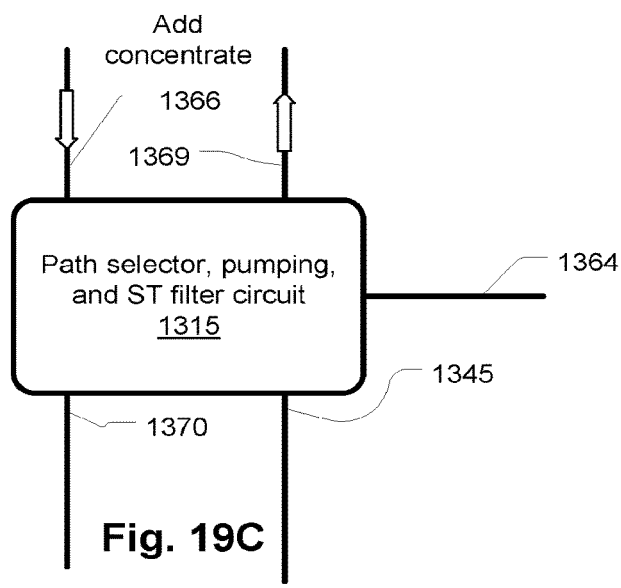
Figure 19D:
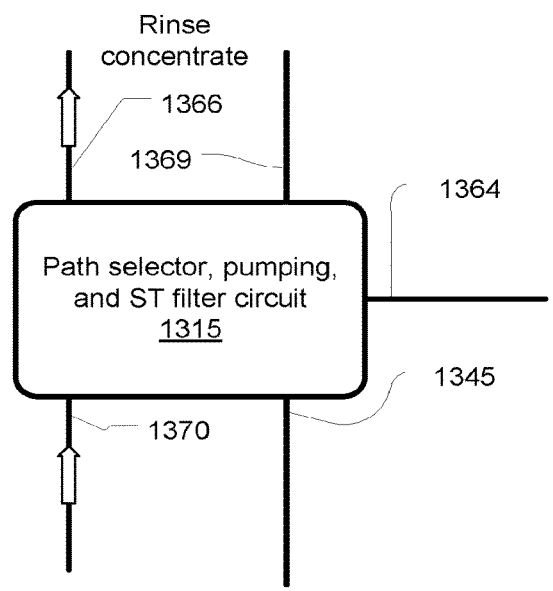
Figure 19E:
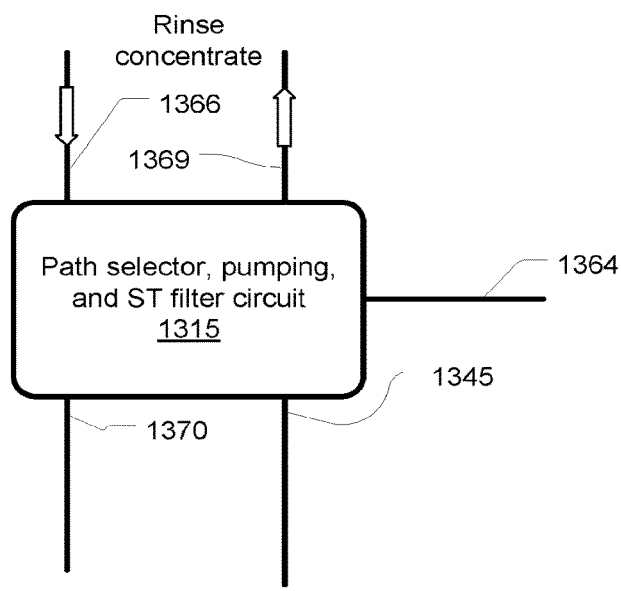
Figure 19F:
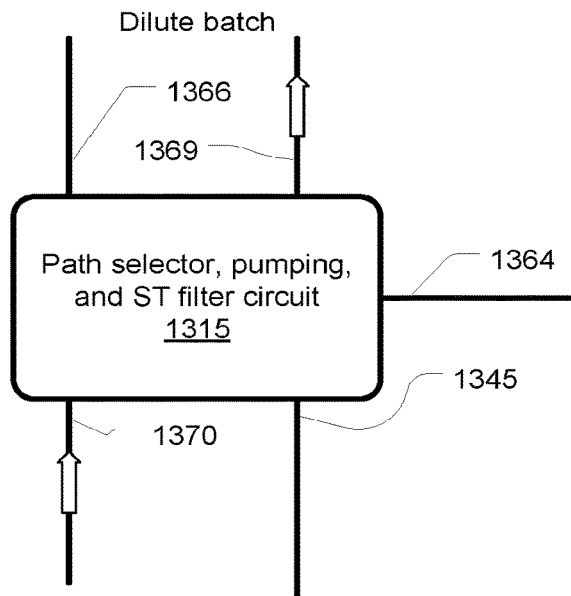
Figure 19G:
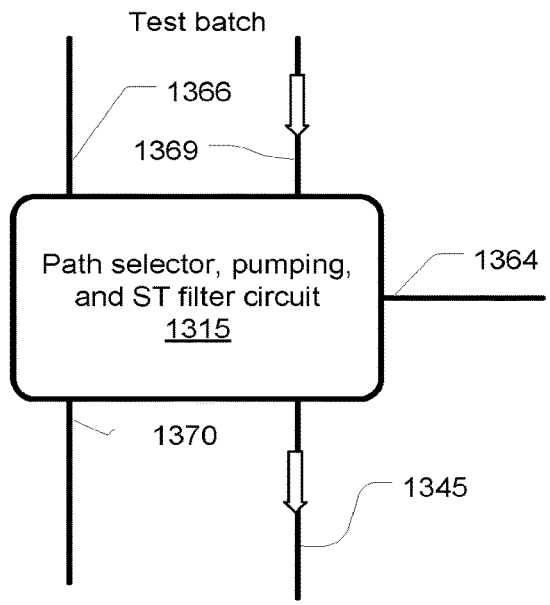
Figure 19H:
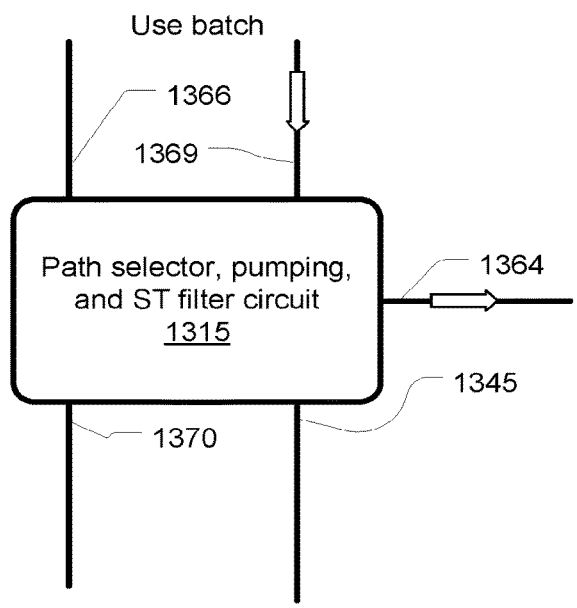
Figure 19J:
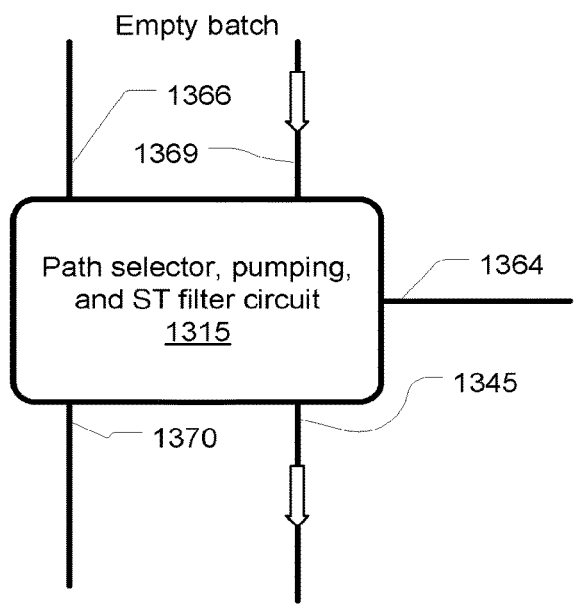

A pump and one or more actuators in operative association with the path selector, pumping, and short term filter portion 1315 may be provided in various configurations to move fluid between selected lines among lines 1366, 1369, 1370, 1345, and 1364. An example of a pump and actuators is discussed below with reference to FIG. 23. Referring to FIGS. 19B to 19H, by moving fluid 5 between selected lines among lines 1366, 1369, 1370, 1345, and 1364 the between selected lines among lines 1366, 1369, 1370, 1345, and 1364 may perform various operations as follows.
1. As illustrated in FIG. 19B, the path selector, pumping, and ST filter circuit 1315 may provide for prefilling the batch container 1317 with purified water by pumping filtered water from feed line 1370 to line 1369 of the path selector, pumping, and ST filter circuit 1315. The pumping may be performed by the metering pump of the pretreatment pumping module 1285 and/or by means of a pump in the path selector, pumping, and ST filter circuit 1315 portion. The transfer of a predetermined quantity may be established by weighing the batch container, by summing the quantity transferred by the metering pump 1029 (FIG. 7), by an optical or mechanical level detector in operative association with the batch 5 container 1317, etc. The quantity in the batch container 1317 may ensure that concentrate is well-mixed in the completed batch and may avoid the need for mixing of the diluted treatment fluid within the batch.
2. As illustrated in FIG. 19C, the path selector, pumping, and ST filter circuit 1315 may provide for the transfer of fluid between lines 1366 and 1369 to transfer concentrate from the concentrate container 1310 to the batch container 1317. The concentrate may be pumped or siphoned.
3. As illustrated in FIGS. 19D and 19E, the path selector, pumping, and ST filter circuit 1315 may provide for repeated cycles of diluting the concentrate in the concentrate container 1310 and transferring rinsed 5 concentrate to the batch container 1317. This may be done by transferring fresh purified water to rinse the concentrate container 1310 by flowing water from line 1370 to line 1366 (FIG. 19D) followed by transferring diluted concentrate from line 1366 to line 1369. These steps may be performed repeatedly until a specified number of cycles of dilution 0 and transfer are completed. The number of cycles may be determined experimentally as sufficient to ensure a repeatable quantity of concentrate is transferred or a certain maximum quantity of concentrate remains in the concentrate container 1310. Preferably, the concentrate is provided in a rigid container that may be effectively rinsed by the above process. Other types of container may be used, however, such as hangable medical fluid bags, solute cartridges, etc. Also, preferably the concentrate is one that permits long term storage as a prepared treatment fluid for dialysis. Note also that instead of a single component concentrate, a multi-component acid component can be mixed with a dry bicarbonate component and used with the present system, particularly if used for acute care and the storage term is limited suitably or other means, such as mixing of the batch, are employed to avoid precipitation which may attend the use of mixed bicarbonate-based treatment fluid. Other alternatives are possible and are not excluded from the scope of invention.
4. As illustrated in FIG. 19F, the path selector, pumping, and ST filter circuit 1315 may provide for the transfer of fluid between lines 1370 and 1369 to transfer purified water to the batch container 1317 and complete the dilution of the batch.
5. As illustrated in FIG. 19G, the path selector, pumping, and ST filter circuit 1315 may provide for the transfer of fluid between lines 1369 and 1345 to transfer fluid from the batch contain 1317 to the quality sensor 1322 to test the quality, for example, the conductivity of the completed batch.
6. As illustrated in FIG. 19G, the path selector, pumping, and ST filter circuit 1315 may provide for the transfer of fluid between lines 1369 and 1364 to make the fluid in the batch container 1317 available to a treatment device such as treatment machine 1312.
7. As illustrated in FIG. 19J, the path selector, pumping, and ST filter circuit 1315 may provide for the transfer of fluid between lines 1369 and 1345 to transfer fluid from the batch contain 1317 to the drain 1397 junction to empty the batch container 1317. This may be done if the batch expires 5 before being used or the entire contents of the batch are not required or for other reasons.

In an alternative embodiment, the steps of 19B, 19C, 19D, 19E, and 19F may be omitted by providing concentrate in the batch container 1317. Another means of transferring the required solute, such as dry solute, may also be provided according to various mechanisms in the prior art which do not require rinsing, such as an inline medicament cartridge (See, for example, Jonsson, et al.: U.S. Pat. No. 4,784,495).

As mentioned, the system 1399 of FIG. 19A may provide batch preparation and storage as well as monitoring functions and support for 5 treatment systems. In an embodiment, in overview, the functions that may be provided are shown in the state diagram of FIG. 20A. From a standby state, the system may initialize the LTF module 1305 (S172) by priming it and testing its performance. The latter step may involve the replacement of the LTF module 1305 and in a preferred embodiment would be done on a schedule ranging from monthly to four times per year depending on the precise capacity of the LTF module 1305. The system may perform the functions of creating a batch S174 and holding a batch while maintaining its temperature S176. The system may make the batch available for use by providing the fluid at a predefined pressure S178. Further functions of draining the batch container 1317 in step S180 and unloading the batch container 1317 by disconnecting in step S182 are also provided.

FIG. 20B shows a typical flow attending normal usage of various the embodiments of a batch preparation and storage system according to various exemplary embodiments described herein. Initially, assuming the system 1399 has been fitted with the components of the permanent portions such as a pretreatment module 1295 and UV/pump module and all controls are in working order, the typical routine provide a new LTF module 1305 at step S135. Then a new batch container 1317 and STF circuit 1315 may be installed and filled at step S130. The batch may be held until required at step S99. Heating may be performed during both steps S130 and S99. Periodically, or when a user attempts to use a batch, at step S100, the system (e.g., 1399) may determine if the batch is near a point of becoming unusable. This may be established by testing or by determining if it the current time since the batch was created is near a protocol limit (e.g., >T1-N hours) and if so a warning may be generated S120. The amount of time that establishes whether a warning may be generated may be determined based on the duration of a treatment, plus a safety margin. In an exemplary embodiment, the warning interval is 8 hours so that if a batch normally is considered to be expired 72 hours after creation, the warning would be given 64 hours after creation. The warning allows the user of the system to use an existing batch rather than allowing it to expire and then being required to make a new one before being treated.

The warning generated at step S120 may correspond to a conventional annunciator such as a bell or it may be an automated web server that generates an email, IM message, cellular SMS, cellular voice message, pager alert, or any other suitable message rendering service. The lead time before which the alert will be generated may made a user-selectable period.

In step S105, it is determined if the batch retention period has expired, requiring a new batch to be generated. If the batch has expired, or if there is insufficient time before expiration to make normal use of a batch, a warning message to that effect may be generated as indicated by the dotted lines. The message may or may not be provided. If the batch has expired, or if there is insufficient time before expiration to make normal use of a batch, control step S125 is performed. If not, a treatment may be performed S110. If the batch is depleted S140 or a treatment count on a stored batch is reached S115 (these may be alternatives in a given embodiment or both tests may be done), control proceeds to step S125.

At step S125, the system may determine if the LTF module has expired as indicated by a test or by an elapsed time period or both. If the LTF has expired, control returns to step S135 and if not, it is determined if the batch container needs to be drained. If so, the batch container is drained and removed and, in either case, control then proceeds to step S130.

At any point in the control flow, various system tests may be performed. One of the more important is the testing of the quality of water purification performed by the LTF module. In step S142, which may be performed, essentially, at all times, if the LTF module is determined to be near expiration, as discussed with regard to the resistivity probe 1022 in FIG. 8A. In such a case a status (stored as a semaphore in a memory of a controller, for example) of the LTF module may be updated to prevent its use after a current batch is completed. This status may be interrogated in step S125 and used to determine if the LTF module is expired. Step S142 represents both the continuous test of the LTF module condition as well as the step of updating the status if the condition warrants. Also at any point, a breakthrough of contaminants in the LTF module, for example sensor 1025 (FIG. 8A) may indicate the instant expiration of the LTF module at step S144. In that case, step 144 includes the initiation of safeguard procedures such as shutting down of pumps and/or the generation of alarms. Again, alarms may be of any sort, including wireless or web-based messages to users, service providers, treatment supervisors, etc.

Figure 21A:
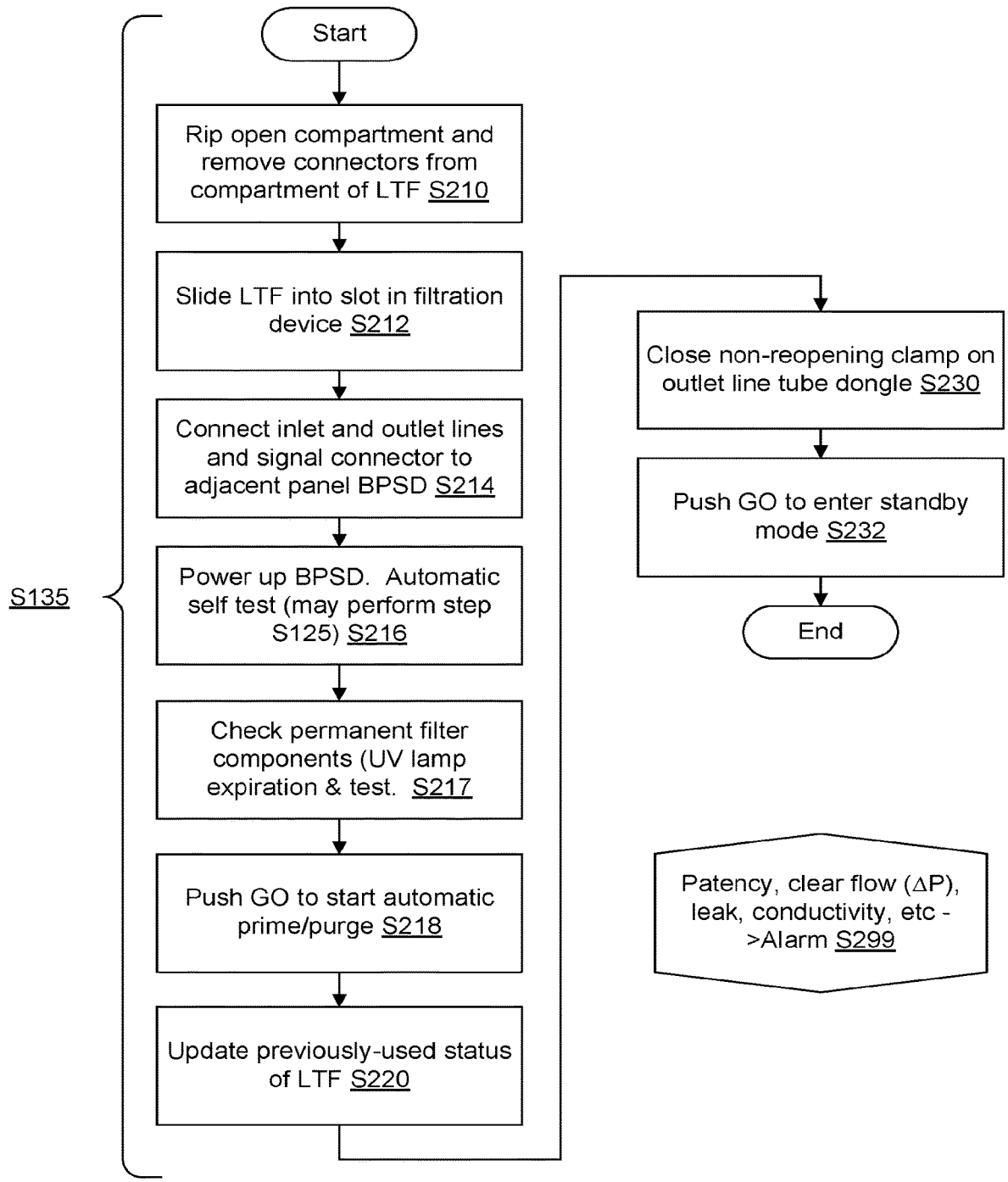
FIGS. 21A to 21C illustrate details of the operation of FIGS. 20A and 20B.
Figure 21B:
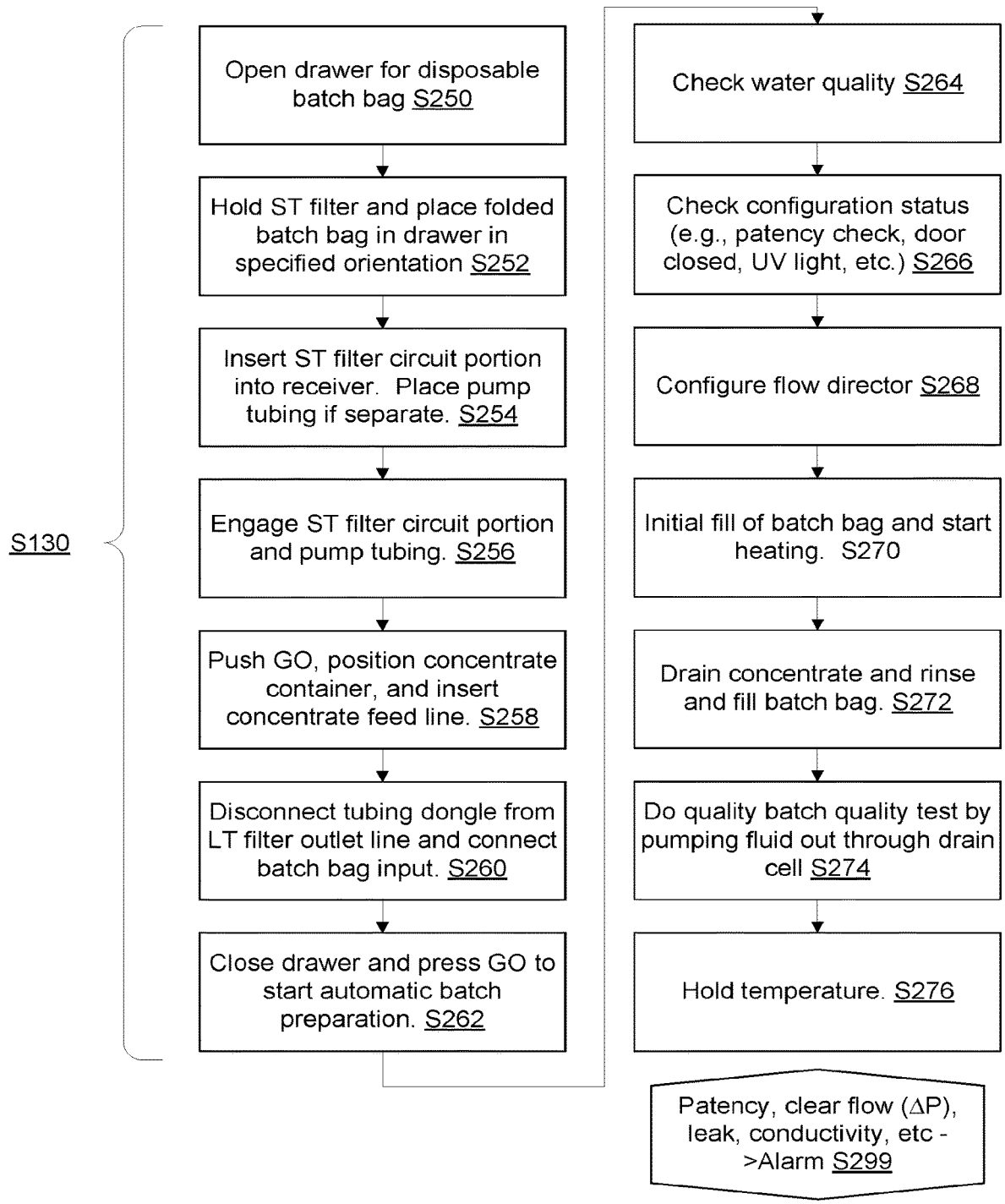

Step S135 may include the steps shown in FIG. 21 A. The LTF module may be housed in a cardboard container provided with an openable compartment where all connectors, including electrical and tubing connectors, are collected and fed out. In step S210, the compartment, for example in a housing of cardboard, may be ripped open and connectors removed. The LTF module may then be put in place, at step S212, in the filtration and storage device (e.g., 1399) and connections for inlet and outlet lines and electrical connections, which may be provided on a unitary filtration and storage device as described later (FIGS. 24 and 27) may be made at step S214. The filtration and storage device (abbreviated in the drawings as BPSD for "Batch Preparation and Storage Device") may be powered up at which point at step S216, a controller may perform a sequence of self-tests including testing the UV lamp (if present), expiration (LTF module is previously used or unauthorized as discussed above), and other tests. At step S218, a user may press an actuator ("GO" button) of a user interface to start an automatic prime and purge sequence which may involve flushing the LTF module sufficiently to remove any residual agents used in manufacture of components and the clearing of any air as well as priming. The latter may be done automatically At step S230, after the system as finished with the prime/purge sequence of step S218, a non-reopening clamp on a dongle (similar to 1361, FIG. 19A) pre-attached to the LTF module and left in place until a new batch bag and short term filter circuit is connected as described further below. Then user may press the actuator ("GO" button) of the user interface to enter the standby mode S232.

During the above procedures, the system may at any point (indicated by step S299), for example after fluid connections are completed, perform pressure test to determine if there are any leaks. In this case, a pump may be run (e.g., 1029, FIG. 7) to create a pressure and then the pressure monitored for an interval to see if the relief rate corresponds to one previously determined to indicate a leak. Similarly pressure may be measured during the purge step of S218 to ensure no blockages are present as indicated by a high back pressure or an overly low backpressure which may indicate a faulty seal or filter medium. If any out of bounds conditions are found, step S299 includes the generation of a corresponding indication or alarm.

FIG. 21 B shows details of step S130 of FIG. 20B. As discussed further below, the batch container 1317 may be provided as part of a disposable component with preconnected tubing, short term filter, sensors, seals, clamps, etc. The container itself may take the form of a large bag which may be shipped in a folded condition such that if laid properly in a container and filled, will unfold and expand in a predictable manner. Also, as discussed below, a support container for a large bag may take the form of a rectilinear box 1630 on drawer glides 1614 (FIG. 24). So the first step in installing the container and tubing set disposable may be to open such a drawer and to lay the bag at the bottom in a specified orientation with the tubing and connector portions fed to an accessible location. The tubes may be temporarily wrapped together around an easy to identify component such as the ST filter 1510 (FIG. 23) so that if the user holds that part, the tubes are secured from tangling and positioned in a predictable manner. See steps S250 and S252.

An alignment and retainment mechanism may be provided to secure the tubing and ST filter, for example one is described below with reference to FIG. 23. One or more steps within step S254 may provide for the alignment of the circuit with actuators, pumps, sensors, etc. and then, in step S256, these may be engaged such as by clamping or securing one or more actuator components. Examples of the mechanical aspects are discussed below. Once the circuit is secured, the user may place the system in a mode for connecting the concentrate container. This step may set any valves in position to prevent premature siphoning before the system is prepared for the transfer of concentrate to the batch container. This is done in step S258. The tubing dongle that protects the outlet of the LTF module is then removed in step S260 and the outlet from the LFT module is connected to a connector for the ST filter and batch container circuit. This connection corresponds to, for example, FIG. 19A reference numeral 1344Q. The circuit 1303 may contain a new dongle with a non-reopenable clamp 1740 which may be used later to protect the LTF module after the batch container and ST filter circuit 1303 unit is removed.

Next, at step S262, the user may invoke a batch preparation procedure, according to the current user interface by pressing GO. The procedure may begin by checking water quality S264 using the resistivity sensor 1322 (FIG. 19A) by pushing a test sample out the waste junction 1397. The system may then, at step S266, perform pressure test to determine if there are any leaks. In this case, a pump may be run (e.g., 1029, FIG. 7) to create a pressure and then the pressure monitored for an interval to see if the relief rate corresponds to one previously determined to indicate a leak. Also checked are high back pressure or overly low backpressure which may indicate a faulty seal or filter medium. The condition of a UV light source, if present may also be checked by means of a light sensor. This step S266 may be performed at other points as well.

Figure 23:
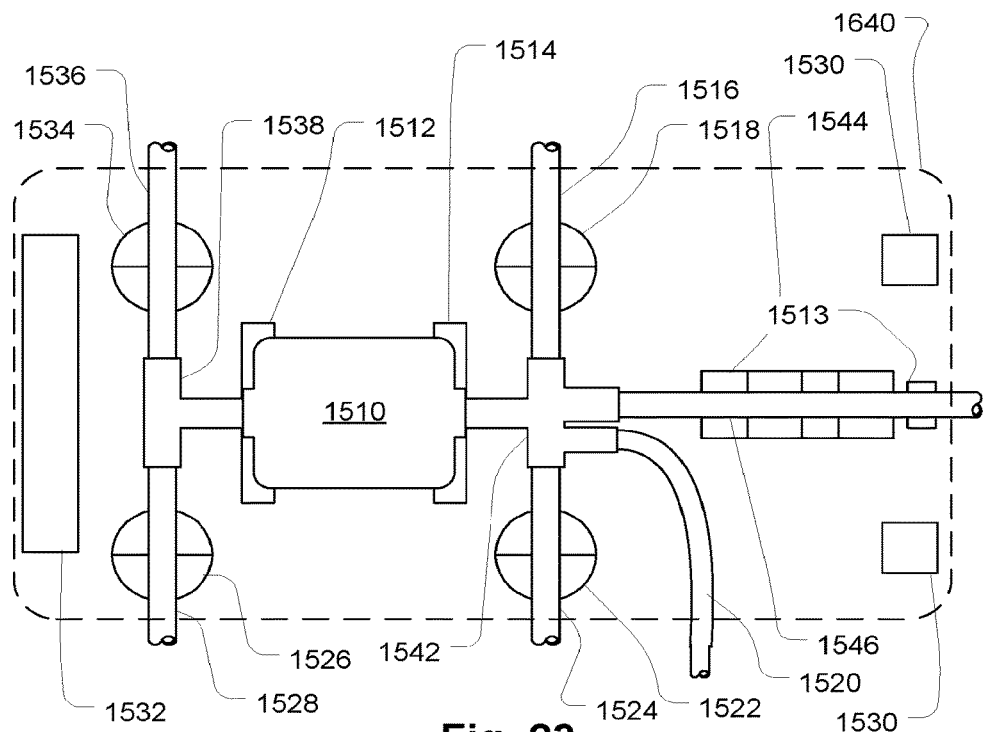
FIG. 23 is a diagram of a flow director.

The flow director (not shown here, but described with reference to FIG. 23, is then configured as described with reference to FIGS. 19B through 19H and 19J in steps beginning at step S268 to provide the functions of adding concentrate to the batch container and diluting to the correct degree. Step S270 corresponds to adding the initial quantity of water before the transfer of concentrate described above with reference to FIG. 19B. Step S272 corresponds to the transfer of concentrate to the batch container described with reference to FIG. 19C and the rinsing sequences described with reference to FIGS. 19D and 19E as well as the final completion of the dilution process described with reference to FIG. 19F. Step S274 corresponds to the fluid quality test, which may include a conductivity test, described with reference to FIG. 19G. The completed batch is warmed and held at a temperature compatible with use beginning at step S276. As above the various out of bound conditions may be tested and confirmed at various points during the process of FIG. 21 B as indicated by step S299.

Figure 21C:
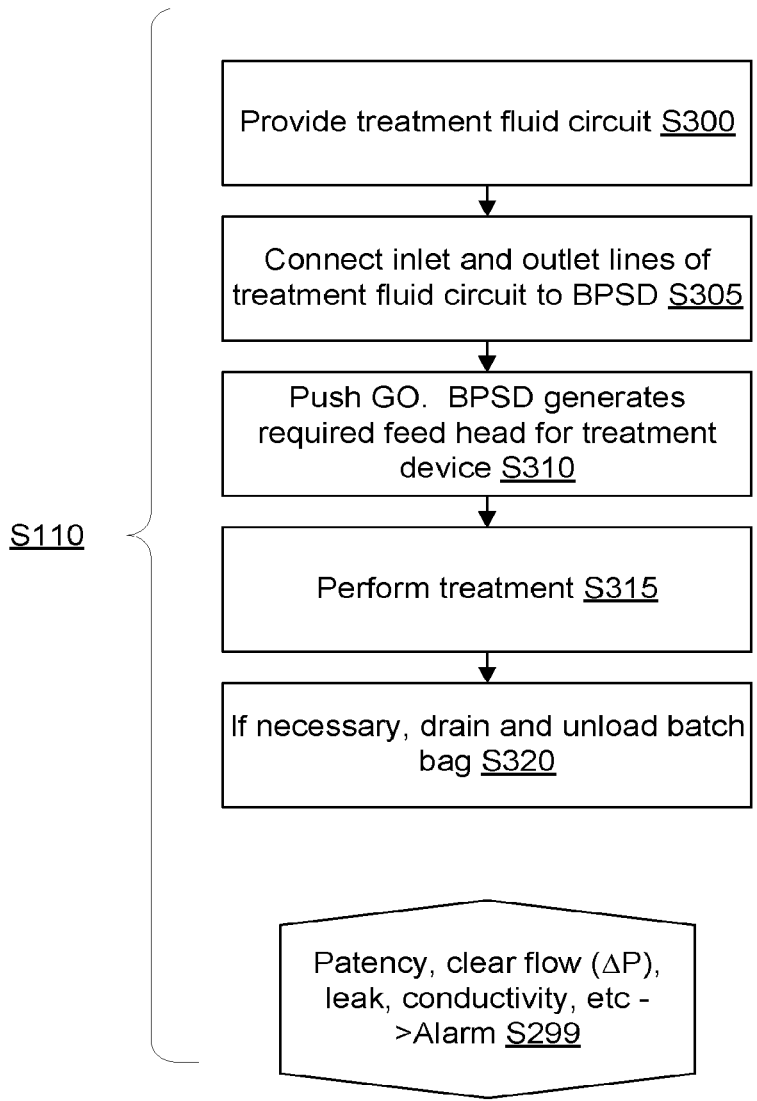

Referring now to FIG. 21C, details for step S110 are indicated which correspond to the process of using a batch of treatment fluid. At step S300, a treatment circuit and/or device is provided. Fresh and spent fluid lines may be connected as required by the particular device in step S305. In the FIG. 27 embodiment described below (for example—true of other embodiments as well), the fresh fluid and waste fluid connections are provided so the connections may be made between the batch preparation and storage device and the treatment device. In step S310, the user may press GO or otherwise place the batch preparation and storage device in a treatment mode in which the system may run a pump to generate a head pressure equivalent to common gravity fed lines that use a hung medicament bag. The batch preparation and storage device may make the fluid available for treatment in other ways as well, for example by simply configuring valves, for example by configuring as described with reference to FIG. 19H. The treatment may be performed using the system as indicated at step S315 and then, if needed, the batch may be drained or the system placed in standby mode where the batch temperature is maintained until the next treatment (step S320). As above the various out of bound conditions may be tested and confirmed at various points during the process of FIG. 21 B as indicated by step S299.

FIG. 24 is a more detailed description of a batch preparation and treatment system which is consistent with the embodiment of FIG. 19A. A pretreatment module 195 receives water from a source, such as a sink faucet 1379, and a UV/pump module 1300 may provide a semi-permanent pre-filtration process as described with reference to FIGS. 6 and 7. The water quantity requirements are preferably such that ordinary household supplies are adequate—as will be observed, the preferred embodiments described permit this. The connection to a sink faucet may be by way of a common connector that replaces the aerators of many household faucets. A long term filter (LTF) module, for example, 1305 provides water purification for multiple multi-treatment batches, for example sufficient for daily treatments for 30 days. In a preferred embodiment, the LTF module 1305 includes KDF, segregated SAC/SCA bed deionization (DI), and mixed bed and ultrafiltration as described with reference to FIGS. 2A and 8A. The LTF module, as also described above, may be in the form of a completely disposable module which only requires a small number of connections to replace. Various connectors are omitted from FIG. 22 because their description is not necessary. Like numerals (in FIGS. 19A and 22) specify similar components so their description is not duplicated here.

A particular example of a path selector, pumping and ST filter circuit 1315 is indicated at 1499. Four valves 1416, 1418, 1414, and 1412 and a pump 1464 are independently controlled by a controller 1497 to provide the selectable paths described with reference to FIGS. 19B through 19H and 19J. The valves are preferably pinch valves that press on medical tubing to open and close. Note that fluid may be prevented from being pumped into the batch container (in the present embodiment a batch bag 1444) by a check valve that has a lower limit requirement before it opens (a "cracking pressure"). So, for example, when water is pumped into the concentrate container 1404, it is not necessarily pumped into the batch bag 1444. The dialysate pump 1464 may also prevent water from being pumped into the batch bag 1444 as well. The following list shows the valve configuration and pump configuration for the modes of FIGS. 19B through 19H and 19J. The forward and reverse pump directions are indicated at 1467 and symbolized by "F" and "R" in the table below. The state of the pump 1464 being off, and thereby acting as a closed valve, is indicated by "X." The valve configurations are indicated by "C" for closed and "O" for open.

TABLE 1

| Flow director configurations | | | | | |
|---|---|---|---|---|---|
| FIG. number | 1418 | 1416 | 1412 | 1414 | Pump |
| 19B | O | C | C | C | R |
| 19C | C | O | C | C | R |
| 19D | O | O | C | C | X |
| 19E | C | O | C | C | R |
| 19F | O | C | C | C | R |
| 19G | C | C | C | O | F |
| 19H | C | C | O | C | F |
| 19J | C | C | C | O | F |

Fluid warmer 1452 may be thermostatically controlled using a temperature sensor 1448. A leak sensor may be provided at a location in the support 1456 for detecting any leaks from the batch bag 1444. A weight scale 1451 may be used as an alternative further means of determining the quantity of fluid transferred to the batch bag 1444. The batch bag may be supplied with concentrate already in it so that the above steps relating to transfer of concentrate from a separate container may be omitted.

The valve assembly may be as shown in FIG. 23, with a pinch actuators 1534, 1518, 1522, and 1536, compressing tubing branches 1534, 1516, 1524, and 1528, respectively against an anvil plate attached to a door (not shown in FIG. 23) that closes over the assembly. The door is hinged 1530 and latches 1532 such that the tubing branches 1536, 1516, 1524, and 1528 are compressed when the pinch actuators 1534, 1518, 1522, and 1536 are activated (moving toward the viewer from the perspective the drawing page). A pump tubing segment 1546 is held against the rollers of a peristaltic pump actuator 1544 by a pump race segment attached to the door. Tubes 1536, 1516, 1524, 1528, 1546, and 1520 in FIG. 23 correspond to lines 1366, 1469, 1345, 1370, 1462, and 1460, respectively, in FIG. 22.

Leak sensors 1486 and 1490 may be provided to detect leaks around or within the corresponding modules 1300 and 1305. A common waste junctions 1434 has connectors 1432 and 1438 for receiving fluid from the batch preparation and storage device and from the treatment device (not shown here, but the corresponding connection is 1344B in FIG. 19A). The conductivity sensor 1428 corresponds to the sensor 1322 in FIG. 19A. check valves 1430 are provided for each branch 1422 and 1431. Extra connectors may be provided for convenient replacement of components as shown.

A branching connector junction 1402 provides multiple connections for the fluid inlet of a treatment device (not shown here). To help ensure against touch contamination, each connector 1742A, 1742B, and 1742C is sealed before use. Each connector is, in turn, unsealed and connected to the inlet line 1745 of the treatment device (as is connector 1742B in the figure) while the other connectors remain sealed (as are connectors 1742A and 1742C). When a treatment is completed, a non-reopening clamp 1740 of the previously used connector (1742B) may be closed and the treatment device inlet line 1745 may be disconnected. This prevents any incursion of contaminants back into the fluid circuit or batch bag 1444. Alternatively, a check valves may be used in a single branch, but the positive seal provided by this multi-branch connector junctions 1402 is preferred.

To provide a stable and predictable source fluid pressure, similar to that provided by a fluid bag hung above a treatment device, in a situation where the batch container is below the treatment machine as it is in the preferred embodiment (See FIG. 25), a recycling loop 1462 and 1460 is provided. When the pump 1464 pumps in the forward direction, any resistance forces fluid backward through the check valve 1472, which is characterized by the above-identified cracking pressure. An exemplary pressure is 3.5 psi. Thus, during treatment, the pump 1464 runs continuously feeding fluid back into the container while the line 1469 remains substantially at 3.6 psi. If the line 1369 ascends a substantial distance, the pressure may be lowered and the final pressure "seen" by the treatment device may be provided at any desired value.

FIG. 23 illustrates an embodiment of the user interface/door 1640 which may provide a surface against which the valve actuators 1534,1518, 1522, and 1536 operate and may position a pump race against the rollers of peristaltic pump 1544. A convenient mechanism for positioning the four tube portions 1536, 1516, 1524, 1528, 1546, the short term filter 1510 provides a rigid casing that supports junctions 1538 and 1542. The casing of the short term filter 1510 may be positioned and engaged in a holder, for example as indicated by brackets 1512 and 1514, to align the entire assembly. A support 1513 for the pump tubing portion 1546 may also be provided. A more extensive fixture may be used such as vacuum molded tray to hold the pump tubing portion 1546 as well as the our tube portions 1536, 1516, 1524, 1528, 1546 and the short term filter 1510 could also be provided so that loading is simplified.

FIG. 24 illustrates a preferred configuration for the batch filtration and storage device 1600 consistent with the embodiments described above. A unitary cabinet 1601 is provided with utility connections in back (not shown) for water supply and draining, and AC electrical feed. A drawer 1630 holds the batch bag 1444. tubes may be fed out of the drawer 1630 and directly behind the user interface door 1640. The tubes that connect to the treatment device, positioned on top of a table 1612 surface, may be fed through a notch 1641 to the treatment device. An example of a treatment device 1660 sitting on the table surface 1612 is shown in FIG. 25. The LTF module 1624, and also shown in FIG. 26, slides into a corresponding space within the cabinet 1601. A compartment 1626 can be opened (this may be done before inserting the LTF module 1624) and connectors of the LTF module 1624 conveniently mated to connectors 1632 on the batch filtration and storage device 1600. The embodiment of FIG. 24 has a separate pump portion as indicated at 1602. The UV/pump module 1300 may be located in a horizontal configuration as indicated at 1616 and slidable out of the cabinet. A door 1610 allows the majority of the units internals to be concealed during operation and a port 1608 provides access to the control panel 1604 built into the user interface door. An additional door 1622 covers the LTF module 1624. Wheels 1618 may be provided to permit the unit to move around.

The packing of the components of the LTF module 1680 according to an embodiment thereof, is illustrated in FIG. 26. The carbon/KDF module 1007 SAC/SBA cartridges 1002A-1002C and the mixed bed DI module 1031 described with reference to FIG. 8A are arranged in flat array as indicated at 1624. The various resistivity sensors 1684 and the ultrafilters 1682 and air filters 1688 (corresponding to 1035A and B and 1047 in FIG. 8A) are also arranged in the same plane. Connectors and lines fit into the compartment area 1686.

Figure 27:
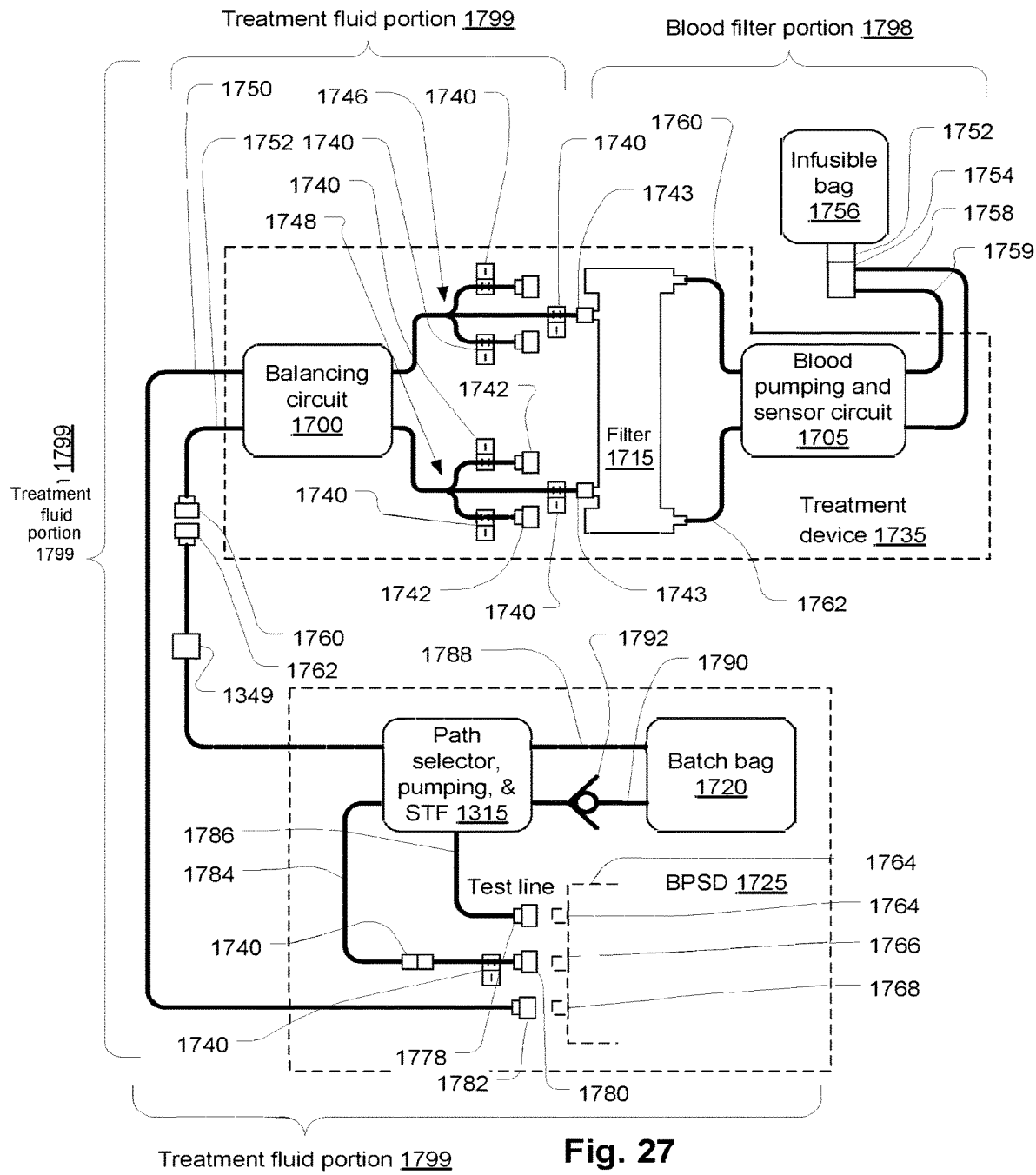
FIG. 27 is a circuit diagram illustrating features of a treatment fluid preparation and storage device according to an embodiment of the invention.

Referring to FIG. 27, a fluid circuit configuration for the treatment device allows for separate blood and dialysate circuits in a dialysis embodiment. Since the treatment fluid batch can be retained and stored for a period of days, it may be convenient to provide a fluid circuit that is retained for the same period, necessitating the exchange of only the blood portion of the circuit. This may simplify set up, reduce the risk associated with improperly installed components, and reduce cost somewhat. Here, the treatment device is indicated at 1735 and the Batch preparation and storage device at 1725. The batch bag is indicated at 1720. The check valve 1792 that provides the head pressure to feed the treatment device 1735 from below the treatment device 1735, as illustrated in FIG. 25, and feed line 1788 are also shown. The path selector circuit portion 1315 is described above and may be according to any of the embodiments or others. Other lines 1786, 1784, and connectors 1740, 180, 1782, 1762, and 1778 and the lines connecting them to the path selector circuit portion 1315 may be pre-connected to a balancing circuit 1700 that forms part of the treatment device 1735. Respective mating connectors 1764, 1766, and 1768 on the batch preparation and storage device 1725 may be provided such as indicated in FIG. 24 at 1632. The balancing circuit 1700 may be a volumetric balancing circuit as described in U.S. Pat. No. 6,638,478 which is hereby incorporated by reference as if fully set forth in its entirety herein. A blood filter circuit portion includes a filter (e.g. a dialyzer) 1715, blood lines 1760 and blood pumping and sensor circuit 1705, venous and arterial lines 1758 and 1759 and possibly other components. The venous and arterial lines 1758 and 1759 are shown connected to an infusible fluid bag 1756 for priming of the blood circuit which may be done with an infusible fluid delivered in the infusible fluid bag 1756. A double connector 1754, 1756 may be provided to allow fluid to be circulated through the infusible fluid bag 1756 allowing gases to settle out.

Note that the batch preparation and storage device may provide fluid for priming the blood circuit by pushing treatment fluid through the blood circuit filter 1715 into the blood circuit 1705 and into the infusible bag 1756. In this case, the infusible bag may be provided as part of the blood circuit 1705 and preattached as illustrated. Note also that it is contemplated that a patient access would be connected in some appropriate fashion after priming is completed by disconnecting the connectors indicated figuratively at 1752 and 1754.

Figure 22:
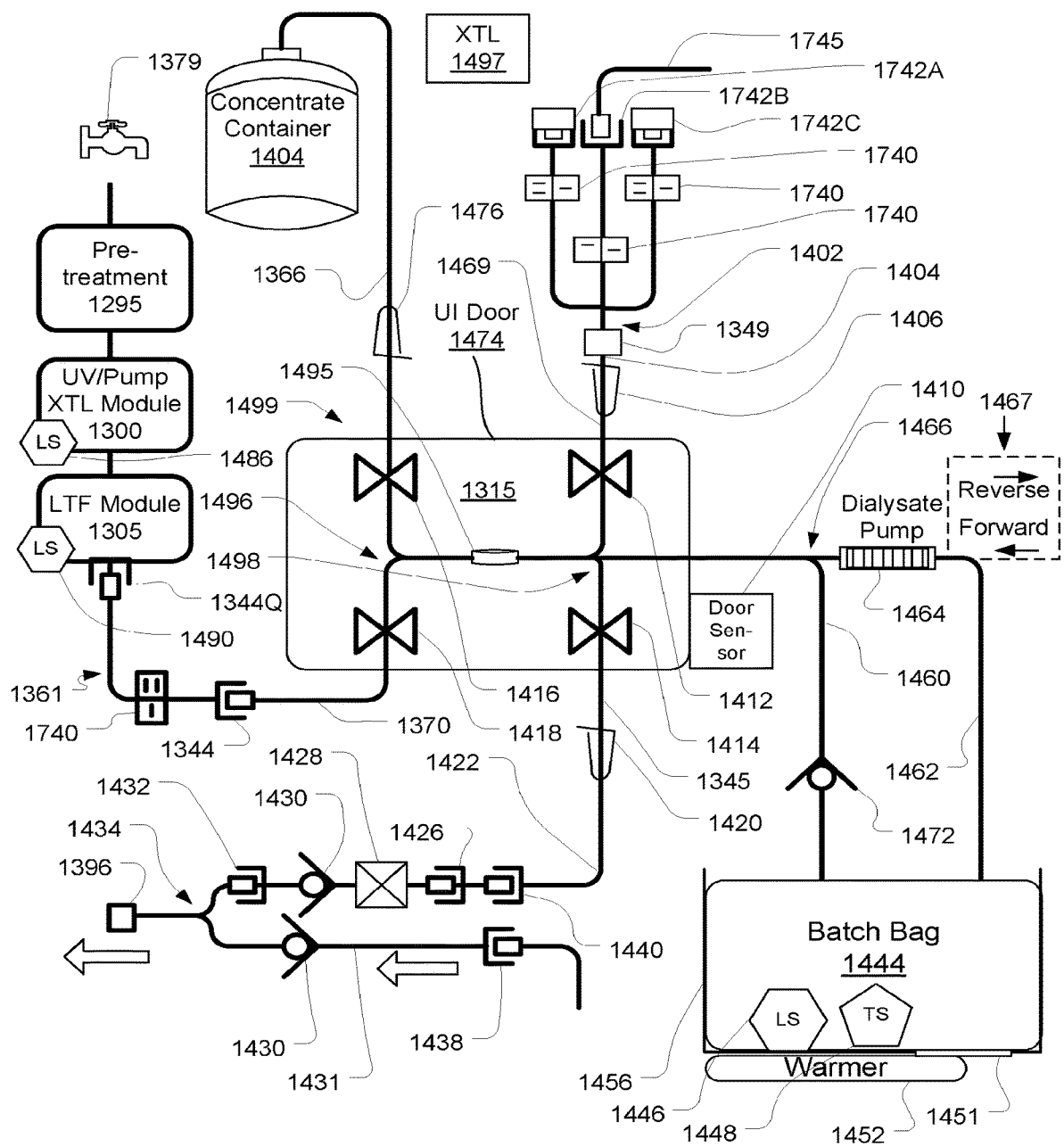
FIG. 22 is a circuit diagram illustrating features of a treatment fluid preparation and storage device according to an embodiment of the invention.

A multiple connector 1746 may be provided which is the same as, and used in the same manner as that indicated at 1402 and described with reference to FIG. 22. For each treatment, the blood filter portion 1798 is replaced after the treatment is completed. The non-reopenable connector 1740 of the used connector among those indicated at 1746 and those indicated at 1748 is closed and the blood filter portion 1798 disconnected by disconnecting the connectors 1743 of the filter 1715. However, the treatment fluid portion 1799 can remain in place.

Figure 28:
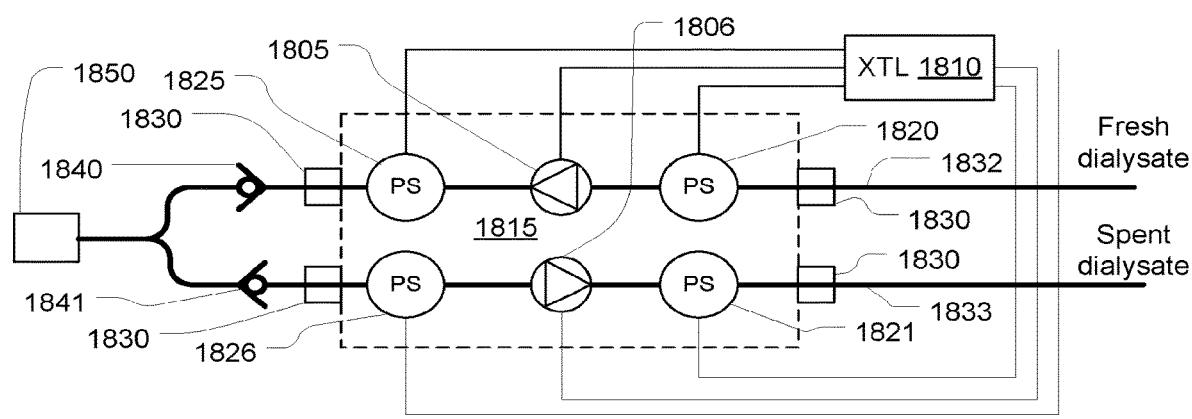
FIG. 28 is a diagram of a compact peritoneal dialysis cycler.

Referring to FIG. 28, a peritoneal dialysis device is shown. One feature of the convenient design of the batch preparation and storage device embodiments of FIGS. 22 and 25 is that they permit convenient connection to a variety of different kinds of treatment equipment. For example, instead of a full hemodialysis treatment and circuit as described with reference to FIG. 27, the batch preparation and storage device 1600 may be employed with a peritoneal dialysis cycler, an embodiment of which is illustrated in FIG. 28. The fresh and spent dialysate lines 1832 and 1833 may be connected to the batch preparation and storage device (any embodiment) as, for example, the corresponding lines 1372 and 1362, respectively, of the embodiment of FIG. 19A. Pumps 1805 and 1806 may be controlled by a controller 1810 using feedback control based on inlet and outlet pressure sensor readings from pressure sensors 1820, 1825, 1821 and 1826, respectively. In addition, precise inlet and outlet pressure readings combined with a calibration curve for each pump may allow the precise determination of total volume of fluid transferred to and from the patient. Using such a calibration curve approach may permit such a peritoneal dialysis cycler to use a compact unit using a peristaltic pump while providing high precision in metering dialysate for treatment.

As is known, peritoneal dialysis can only be used up to a point in time after which the peritoneum cannot be used effectively for treatment. After this happens, patients must switch to normal dialysis, for example using an extracorporeal treatment system. However, for many patients, peritoneal dialysis is preferred and such patients may wish to use peritoneal dialysis for a period of time, and later switch to normal dialysis. Another alternative is for patients to use both peritoneal and normal dialysis at different times, giving them flexibility and potentially extending the term over which the peritoneum can be used for treatment. In such cases, as described below, convenient switching between the types of treatment machines may be facilitated with a batch preparation and storage device as described herein.

A peritoneal cycler according to the design of FIG. 28 (or other designs) may be configured to rest on a table top. The design of the batch preparation and storage device of FIG. 25 permits such a peritoneal cycler to be used until extracorporeal blood treatment is indicated at which point, the peritoneal cycler can be exchanged for an extracorporeal blood treatment device such as shown in FIG. 25. No change is required in the batch preparation and storage device 1600.

Note that the embodiments of FIGS. 19A through 19H, 19J, and 20 through 28 are contemplated as being able to employ the data carrier and data carrier reader devices, described above with reference to earlier figures, for enforcing the expiration of replaceable components such as the LTF modules, ST filter and fluid circuit modules, etc. of the foregoing embodiments or the treatment circuits. In addition, the same data carrier devices may are contemplated for use in preventing re-use of previously used replaceable components.

The controller for the batch preparation storage and treatment devices above may provide a treatment scheduler that takes into account the permitted storage term of the batch and the time the batch is created or proposed to be created. Such a scheduler may accept as inputs, the times during which the patient wishes to perform treatment and the scheduler may, in response, calculate and display the window of time during which the batch should be prepared for it to be ready during those treatment times and still be available at the last treatment time. This calculation may take into account the time it takes to prepare a batch, the length of time before the batch expires, estimates of how long it takes a patient to set up a treatment and allowances for pausing treatments and other information. Alternatively, the scheduler may accept a time when a batch is proposed to be prepared and then output proposed treatment times, taking into account the type of treatment (daily or longer intervals), the intensity of treatment, size of batch, etc. The schedule may retain the schedule and make it available on a wireless device, providing reminders, etc. for the various tasks to be timely performed according to entered schedules. In a preferred embodiment, the scheduler is provided by a server application accessible through the web. The scheduler, may be a local application, a server application, or split between a server and a thin client application (the client application running on the treatment controller). The application may actually control the system to begin the preparation of the batch at a scheduled time. In the latter case, the batch container and circuit may be pre-connected to the batch preparation and storage device and so that the system can then automatically start the preparation at a scheduled time. Still further, if any problems are encountered, the scheduler system may alert the patient or other responsible person of the problem so that ameliorative actions may be taken.

Note that although in the above embodiments, the treatment regimen emphasized may have been daily treatment with moderate clearance, it should be clear that the batch preparation and treatment device and other inventive embodiments described are consistent with other treatment regimens.

Although the foregoing inventions have, for the purposes of clarity and understanding, been described in some detail by way of illustration and example, it will be obvious that certain changes and modifications may be practiced that will still fall within the scope of the appended claims. For example, the devices and methods of each embodiment can be combined with or used in any of the other embodiments. For another example, the air vents described can be of any suitable description and need not be membrane type air vents at all, although these are preferred.

The invention claimed is:
1. A fluid treatment plant, comprising:
    a filter module that has a unique identifier relative to other filter modules, the filter module including at least a first filter and a second filter connected in series and connectable to a supply of a fluid;

a pump fluidly connected to the filter module and configured to pump the fluid;

a controller with a fluid quality sensor connected to detect a quality of the fluid between the first filter and the second filter;

a filter module detector connected to the controller, the controller being configured to detect the unique identifier of the filter module connected to the pump with the filter module detector, wherein the controller is connected to control the pump responsively to a signal from the fluid quality sensor and the filter module detector, the controller is configured to control the pump to continue pumping if, during a pumping operation, the fluid quality sensor gives a first indication, and the controller is further configured to control the pump to continue pumping until a predetermined quantity of the fluid has been pumped if, during the pumping operation, said fluid quality sensor gives a second indication that is different from the first indication, and after the predetermined quantity of the fluid has been pumped to control the pump to not pump any more of the fluid until said filter module is replaced with a different filter module that has a different unique identifier than the unique identifier of said filter module.

2. The fluid treatment plant according to claim 1, wherein said first and second filters are deionizing filters and said fluid quality sensor is a conductivity sensor.

3. The fluid treatment plant according to claim 1, wherein the first filter is a replaceable filter with a strong acid cation (SAC) filter bed.

4. The fluid treatment plant according to claim 3, wherein the second filter is a replaceable filter with a strong base anion (SBA) filter bed in at least two segregated layers and configured to substantially remove colloidal aluminum from water.

5. The fluid treatment plant according to claim 1, wherein said filter module detector is a data carrier reader.

6. The fluid treatment plant according to claim 5, wherein the controller is configured to download software instructions via said data carrier reader for performing a water treatment operation.

7. The fluid treatment plant according to claim 6, wherein the controller executes the software instructions downloaded via the data carrier reader from a data carrier that is present on the filter module.

8. The fluid treatment plant according to claim 5, wherein the filter module is provided with a data carrier attached to the filter module.

9. The fluid treatment plant according to claim 8, wherein the data carrier is a radio frequency identification device (RFID).

10. The fluid treatment plant according to claim 8, wherein the data carrier is a bar code.

11. The fluid treatment plant according to claim 8, wherein the data carrier contains the unique identifier of the filter module.

12. The fluid treatment plant according to claim 8, wherein the data carrier includes a flag indicating that the filter module is expired.

13. The fluid treatment plant according to claim 8, wherein the controller is configured to prevent pumping of fluid based on the data carrier read by the data carrier reader.

14. The fluid treatment plant according to claim 1, wherein the fluid is water.

15. A treatment plant for preparing purified water for medical use, comprising:

a controller having a data carrier reader that is configured to read a data carrier; and a fluid pump controlled by the controller;

a connector adapted to receive filter modules for purifying water, each filter module having a respective data carrier with a unique identifier, wherein the controller is configured to read the unique identifier of a filter module received by the connector and make a comparison of the read unique identifier to at least one other identifier when the filter module is connected to the connector, and to make a decision to either prevent a water preparation operation or to proceed with the water preparation operation responsively to a result of the comparison.

16. The treatment plant according to claim 15, wherein the data carrier is at least one of a radio frequency identification device and a bar code.

17. The treatment plant according to claim 15, wherein the data carrier stores software instructions to be executed by the controller.

18. The treatment plant according to claim 15, wherein the controller is further configured to control a pump to stop pumping to prevent the water preparation operation.

* * * * *